United States Patent [19]

Verweij et al.

[11] Patent Number: 4,695,627

[45] Date of Patent: Sep. 22, 1987

[54] CEPHALOSPORIN DEOXYGENATION PROCESS

[75] Inventors: Jan Verweij, Leiden; Herman H. Grootveld, Benthuizen; Henri G. J. Hirs; Gerardus J. Van Veen, both of Zoetermeer; Jan Kalter, Hazerswoude-Dorp; Peter W. Henniger, Leiden, all of Netherlands

[73] Assignee: Gist-Brocades N.V., Delft, Netherlands

[21] Appl. No.: 653,866

[22] Filed: Sep. 21, 1984

[30] Foreign Application Priority Data

Oct. 7, 1983 [EP] European Pat. Off. ......... 832014526

[51] Int. Cl.$^4$ .................. C07D 501/20; C07D 501/58
[52] U.S. Cl. .................................... 540/224; 540/215; 540/222; 540/225; 540/226; 540/227; 540/228; 540/229; 540/230; 204/157.7
[58] Field of Search ...................... 544/16, 20, 22, 27; 540/224, 215, 222, 225, 226–230; 204/157.7

[56] References Cited

U.S. PATENT DOCUMENTS

| | | | |
|---|---|---|---|
| 4,044,022 | 8/1977 | Hatfield | 540/221 X |
| 4,223,133 | 9/1980 | Bunnell | 540/222 X |
| 4,258,041 | 3/1981 | O'Callaghan et al. | 540/21 |
| 4,266,049 | 5/1981 | Bonjouklian | 540/16 |
| 4,308,380 | 12/1981 | Kamiya et al. | 540/17 |

*Primary Examiner*—Donald G. Daus, Jr.
*Assistant Examiner*—William A. Teoli
*Attorney, Agent, or Firm*—Bierman & Muserlian

[57] ABSTRACT

A process for the preparation of 7β-acylamino-3-substituted-3-cephem-4-carboxylic acid compounds comprising reacting at −70° C. to 0° C. in an inert organic solvent phosphorus pentachloride with a cephalosporin compound in the presence of an olefinic compound having at least one carbon-carbon double bond having not more than three hydrogen atoms attached thereto capable of removing chlorine at least in part by addition to a carbon-carbon double bond.

37 Claims, No Drawings

CEPHALOSPORIN DEOXYGENATION PROCESS

STATE OF THE ART 1-oxides of cephalosporins and cephalosporin derivatives appear as intermediates in many syntheses of valuable therapeutically active cephalosporins, for instance because oxidation of the sulfur atom of the dihydrothiazine ring facilitates introduction of substituents in other parts of the molecule. In some other syntheses, the double bond in the dihydrothiazine ring is shifted from the 3-position into the 2-position and to restore biological activity, the double bond is isomerized back into the 3-position by mono oxidation of the sulfur atom, followed by removal of the oxygen introduced.

A particularly interesting application of cephalosporin 1-oxides pertaining to deoxygenation of 7β-acylamino-3-substituted methyl-3-cephem-4-carboxylic acid-1β-oxide derivatives is incorporated into a multi-step preparation of 7β-amino-3-substituted methyl-3-cephem-4-carboxylic acids and esters thereof starting from 7β-acylamino-3-methyl-3-cephem-4-carboxylic acid-1β-oxide derivatives, since the resulting 7β-amino-compounds are direct precursors for the preparation of valuable antibiotics, while the starting materials generally can be obtained in an economic way from penicillins available e.g. by large scale penicillin fermentation, by sequentially, oxidation to 1β-oxides of these penicillins, ring enlargement to so-called desacetoxycephalosporins, and mono-oxidation to desacetoxycephalosporin-1β-oxides.

OBJECTS OF THE INVENTION

It is an object of the invention to provide a one step process for the deoxygenation of cephalosporin-1-oxide derivatives in a single step.

This and other objects and advantages of the invention will become obvious from the following detailed description.

THE INVENTION

The novel process of the invention for the preparation of 7β-acylamino-3-substituted-3-cephem-4-carboxylic acid compounds of the formula

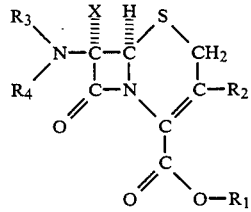

II wherein X is selected from the group consisting of hydrogen, alkoxy of 1 4 to carbon atoms and alkylthio of 1 to 4 carbon atoms, $R_1$ is a hydroxy protective group, $R_2$ is selected from the group consisting of hydrogen, chlorine, methoxy, trifluoromethyl, vinyl, methyl, and methyl substituted by one member selected from the group consisting of: (a) halogen, (b) protected hydroxy, (c) alkoxy and alkylthio of 1 to 4 carbon atoms, (d) alkanoyloxy and alkanoylthio of 2 to 5 carbon atoms, (e) 1-pyridinium optionally substituted with at least one member of the group consisting of cyano, chloro, dialkylamino with alkyls of 1 to 4 carbon atoms, alkoxy of 1 to 4 carbon atoms, alkoxycarbonyl of 2 to 5 carbon atoms, dialkylcarbamoyl with alkyls of 1 to 4 carbon atoms, hydroxy, carboxy, sulfo, and alkyl of 1 to 4 carbon atoms optionally substituted on the first or second carbon atom thereof with a member selected from the group consisting of dialkylamino with alkyls of 1 to 4 carbon atoms, chloro, cyano, methoxy, alkoxycarbonyl of 2 to 5 carbon atoms, N,N-dimethylcarbamoyl, hydroxy, carboxy and sulfo, and (f) heterocyclic thio optionally substituted on ring carbons with at least one member of the group consisting of cyano, chloro, dialkylamino with alkyls of 1 to 4 carbon atoms, alkoxy of 1 to 4 carbon atoms, alkoxycarbonyl of 2 to 5 carbon atoms, dialkylcarbamoyl with alkyl groups of 1 to 4 carbon atoms, hydroxy, carboxy, sulfo, and alkyl of 1 to 4 carbon atoms optionally substituted on the first or second carbon atom thereof with a member selected from the group consisting of dialkylamino with alkyl of 1 to 4 carbon atoms, chloro, cyano, methoxy, alkoxycarbonyl of 2 to 5 carbon atoms, N,N-dimethylcarbamoyl, hydroxy, carboxy and sulfo, and/or on a saturated ring nitrogen atom with alkyl of 1 to 4 carbon atoms optionally substituted on the first or second carbon atom thereof with a member selected from the group consisting of dialkylamino with alkyls of 1 to 4 carbon atoms, chloro, cyano, methoxy, alkoxycarbonyl of 2 to 5 carbon atoms, N,N-dimethylcarbamoyl, hydroxy, carboxy and sulfo, $R_3$ is acyl of an organic carboxylic acid of 1 to 18 carbon atoms and $R_4$ is hydrogen or $R_3$ and $R_4$ taken together with the nitrogen atom to which they are attached form phthalimido comprising reacting at $-70°$ C. to $0°$ C. in an inert organic solvent phosphorus pentachloride with a compound of the formula

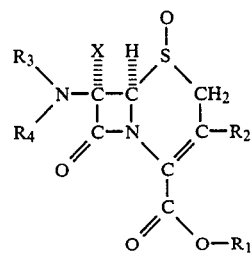

I wherein X, $R_1$, $R_2$, $R_3$ and $R_4$ have the above definition with any hydroxy, carboxy, sulfo and heterocyclic saturated amino groups contained in $R_2$ and $R_3$, optionally being protected by silylation or in the last case also by acylation, in the presence of an olefinic compound having at least one carbon-carbon double bond having not more than three hydrogen atoms attached thereto capable of removing chlorine at least in part by addition to a carbon-carbon double bond.

There are three interrelated one-pot processes for the preparation of 7β-amino-3-substituted-3-cephem-4-carboxylic acid derivatives optionally substituted in the 7α-position from correponding 7β-acylamino-3-substituted-3-cephem-4-carboxylic acid-1-oxide derivatives, of 7β-acylamino-3-substituted methyl-3-cephem-4-carboxylic acid derivatives from corresponding 7β-acylamino-3-methyl-3-cephem-4-carboxylic acid-1β-oxide derivatives, and of 7β-amino-3-substituted methyl-3-cephem-4-carboxylic acid derivatives from 7β-acylamino-3-methyl-3-cephem-4-carboxylic acid-1β-oxide derivatives and all of these one-pot processes comprise an improved process for the deoxygenation of cephalosporin-1-oxide derivatives, which in a single step operation can be applied generally for the deoxygenation of 7β-acylamino-3-cephem-4-carboxylic acid-1-oxide derivatives optionally substituted in the 7α-position. Moreover, the three interrelated one-pot processes are mutually linked so that protection of the cephalosporin-4-carboxyl group by silylation, as introduced in a preliminary step by procedures carried out preferably in situ, can be maintained throughout the whole processes which then do not require isolation of intermediates.

The new process for the deoxygenation of generally cephalosporin-1-oxides can be applied in a broad scope on its own in single step performance or in a somewhat restricted scope as a step participating in multi-step one-pot processes, by using conditions clearly distinct from prior art process conditions, or in a way wherein it improves a prior art process by adding an additional agent while using otherwise also not identical conditions.

One possible way to arrange such a multi-step synthesis of generally 7β-aminocephalosporanic acid derivatives involves the sequence of the following steps:

(a) In view of the necessity to protect the cephalosporin carboxyl group, preparation of a suitable ester of a starting desacetoxycephalosporin-1β-oxide, for many cases preferably as silyl ester in view of relatively easy preparation and very easy removal by hydrolysis afterwards of such an ester group. Very suitably the silyl ester should economically be prepared in situ.

(b) A light induced bromination of the 3-methyl group.

(c) If necessary, dependent to a substantial extent upon the nature of the esterifying group and the character of the acylamino group, selective replacement by hydrogen of bromine introduced additionally in the methylene group adjacent to the sulfur atom in the dihydrothiazine ring.

(d) Replacement of the bromine atom introduced in the 3-methyl group by another atom or group, for instance a variable heterocyclic thio group, wherein the heterocyclic moiety may represent e.g. optionally substituted pyridyl, pyrimidyl, pyridazyl, pyrrolyl, imidazolyl, pyrazolyl, isoxazolyl, oxazolyl, isothiazolyl, thiazolyl, triazolyl, oxadiazolyl, thiadiazolyl, thiatriazolyl and tetrazolyl.

(e) Deoxygenation of the sulfoxy group.

(f) Removal of the acyl group from the 7β-acylamino substituent to give the free 7β-amino group.

It was a leading incentive to this invention to combine and mutually accomodate the individual steps to a one-pot process wherein the need to isolate intermediates could be reduced substantially, eventually preferably resulting in a multi-step synthesis without any isolation of intermediates. A major problem, relating to another but related object of the invention, to reach this target was to find a suitable deoxygenation method for the sulfoxides involved, in particular with regard to the preferred use of silyl protection during the process.

For the object of creating a multi-step synthesis of 7β-amino-3-substituted methyl-3-cephem-4-carboxylic acid derivatives from desacetoxycephalosporin-1β-oxides, which synthesis should turn out to be sufficiently economical in large scale production in comparison to the usual prior art processes comprising substitution reactions applied on 7β-amino-3-acetoxymethyl-3-cephem-4-carboxylic acid (7-ACA) such as the one described in European Patent Application No. 0074316, a suitable candidate for the deoxygenation reaction had to meet at least the following requirments:

(1) The deoxygenation process preferably has to be as amenable to "silicium" esters of the cephem carboxylic acids involved as to their "carbon" esters whereby it will be appreciated by people skilled in the art that successful diligent maintenance of the "silicium esters" during multi-step conversions still is a rare phenomenon in the intrinsically intricate field of β-lactam chemistry.

(2) Whether or not at the same time incorporating the use of "silicium" esters, the conditions of a suitable deoxygenation process, novel or known in the art, have to be mutually adaptable in a smooth way with at least the conditions of the preceding steps necessitating isolation of the product of deoxygenation, and/or the conditions of the last step, which then involves isolation of the product of replacement of the bromine atom in the 3-bromomethyl group. Preferably of course, it should be possible to accomodate all steps to each other so that no isolation of any intermediate is needed, and all steps optionally can be carried out in the same reaction vessel.

However, in view of the individual nature of each of the many sulfoxide-reduction methods known in the prior art, it could not be predicted at all by people skilled in the art beforehand that any of these methods should in fact meet the requirements of a one-pot process, particularly with regard to using silylated intermediates. Furthermore, any interruption involving isolation of an intermediate considerably reduces the advantages associated with using "silicium" esters instead of "carbon" esters.

(3) The yields of the deoxygenation reaction have to be nearly quantitative since the whole process already comprises one step, step (c) that is, of which the conversion yield often is only moderate in the relative sense.

(4) A suitable candidate for the deoxygenation, of which application on single step basis seemed attractive with respect to e.g. reaction temperature, reaction time and chemicals employed has to be applicable in combination with one or more of the other steps of the whole process without undue derivation from such favorable aspects emerging from single step experimentation. If accomodation should appear to require a considerable increase in the use of chemicals, and/or in energy costs such as for instance associated with heavy cooling, and/or in reaction time, that candidate is no longer eligible.

At first glance it may not seem difficult to find and develop a suitable method since the literature clearly indicates a propensity of sulfoxide deoxygenation methods, as in for instance the review article of Drabowitz et al [Org. Prep. and Proc., Vol. 9 (2), p. 63–83 (1977)]. However, many of the general methods and specific procedures indicated therein did not find economical application within the realm of cephalosporin chemistry. For as far as these hardly or even not used deoxygenation methods might perhaps in principle be amenable to develop suitable conditions, such as deoxygenation with zinc in acetic acid and with trichlorosilane, they were tried out in single step application to check whether or not such methods could be compatible with the use of silylated intermediates. They were found to be either not applicable at all, or by far not effective enough, whereby of course expensive methods such as reduction with tributyltinhydride could not be taken into consideration.

Next, the possibility of using methods and procedures known to be effective in cephalosporin chemistry were considered and tried out when assessed to be possibly compatible with one-pot syntheses comprising performance of at least two consecutive steps without isolation of intermediates.

Crowley et al [Tetrahedron, Vol. 39, pages 337–342 and 461–467 (1983)] describe a somewhat similar multi-step synthesis of 7β-amino-3-substituted-methyl-3-cephem-4-carboxylic acid derivatives starting from desacetoxycephalosporin-1β-oxide derivatives, however, while only using "carbon" esters for protection of the 4-carboxylic acid moiety, and whereby consequent on not using silylated intermediates additional bromination of the methylene group adjacent to sulfur may not necessarily be a serious side reaction so that selective debromination does not have to enter the total sequence of steps.

When in said process the acyl group attached to the 7β-amino substituent is not formyl, the indicated deoxygenation method is used only in single step performance. The deoxygenation method employed therein involves as combined agent acetyl chloride to activate the sulfur-oxygen bond and potassium iodide as the reducing agent. Apart from the variation in yields obtained, i.e. 60–90% even in single step performance only, this method is not compatible with the application of "silicium" esters in view of reduced solvability of potassium iodide, of possible reactivity of acetyl chloride towards "silicium" esters at or above room temperature, and of incompatibility of the two solvents used, i.e. of glacial acetic acid which solvent is not suited per se, and of dimethylformamide because of reactivity of this solvent towards phosphorus pentachloride employed in the final step to remove the acyl group from the 7β-substituent.

U.S. Pat. No. 4,044,002 describes a sulfoxide deoxygenation process applicable to various cephalosporanic acid-1-oxides and in general esters thereof, using as the agent of combination of an acyl bromide, e.g. acetyl bromide introduced in at least 100% excess, and a structurally quite variable bromine scavenger which takes up bromine generated in the conversion by addition and/or by substitution. Presumably, mainly for economic reasons the preferred bromine scavengers are simple $C_2$-$C_5$ mono-olefins, although $C_5$-$C_8$ cycloolefins perhaps are equally effective according to the second table of column 12.

In spite of its apparent effectiveness in at least the preferred way of operation, the said process definitely has appeared not to be an attractive point of departure for the development of a suitable and versatile deoxygenation process within the context of the present invention, particularly in view of the indication in said patent of a temperature range which is too high for adaptation to the much more vulnerable "silicium" esters.

It will be appreciated by people skilled in the art that there are various scientific articles concerning the use of generally trivalent phosphorus compounds, in particular phosphorus trichloride and phosphorus tribromide, for the deoxygenation of 1-oxides of penicillins and cephalosporins, such as Claes et al [J. Chem. Soc. Perkin I 932 (1973)], Wright et al [J. Med. Chem. Vol. 14, p. 1420(1971)] and Kaiser et al [J. Org. Chem., Vol. 35 p. 2430(1970)]. Likewise there are a number of patents and patent applications indicating specifically or inter alia successful use of phosphorus trihalides for the deoxygenation of in general "carbon" esters of cephalosporin-1-oxides such as for instance Belgian Pat. No. 737,121.

Although it is not so clear from this prior art that "silicium" esters of cephalosporin-1-oxides too will be amenable to really rewarding deoxygenation by phosphorus trichloride, it was found during single step experimentation that trimethylsilyl esters of at least some cephalosporin-1-oxides could be reduced with phosphorus trichloride in satisfactory yields only when the reaction temperature was kept at about −70° C. or lower. Furthermore, as promonished by the combined prior art, activation of this reducing agent by a relatively considerable amount of dimethylformamide had to be incorporated in the conditions, particularly when using "silicium" esters, unless a considerable excess of phosphorus trichloride was used instead. Such aspects already made the use of such a deoxygenation process in two-steps one-pot conversion of 7β-acylamino-cephalosporin-1-oxides to the corresponding 7β-amino-3-cephem-4-carboxylic acid derivatives too unattractive, furthermore since addition in the second step of phosphorus pentachloride at about −50° C. to a reaction mixture containing much dimethylformamide instead of a considerable excess of phosphorus trichloride by necessity involves heavy cooling and more of phosphorus pentachloride than usual as well.

Relatively heavy cooling and, presumably consequent on remaining amounts of agents introduced before, considerably more reagent than usual (phosphorus trichloride in this case) also resulted from attempts to combine in one-pot synthesis the deoxygenation step with the preceding steps of the overall process, so that the complete one-pot process aimed at comprising no isolation of intermediates became too remote for consideration.

In the hope of finally finding a suitable deoxygenation method of which incorporation in two-step or multi-step one-pot synthesis intrinsically could involve less accommodation to other steps, attention was directed to another method, which in the general sense relates to the use of phosphorus pentachloride as the reduction means since that agent is also used preferably in the final step of the total sequence. According to various indications in the prior art, phosphorus pentachloride in this respect has been used repeatedly in two closely interrelated modifications, both of them comprising removal of chlorine from the reaction mixtures by way of substitution of a simultaneously introduced tertiary amine with simultaneous generation of hydrochloric acid forming a salt with the chlorinated tertiary amine. The corresponding reactions are as follows:

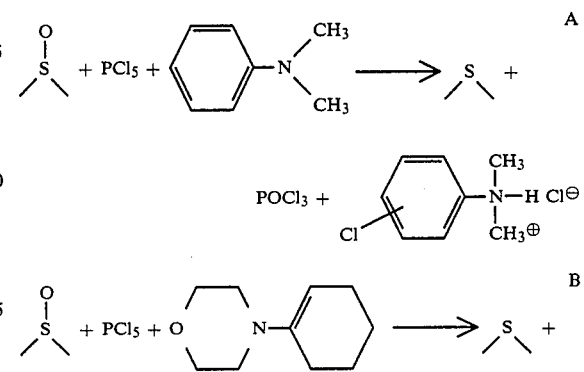

-continued

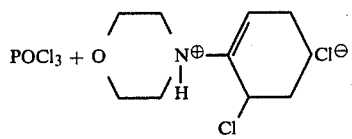

Although both interrelated methods are sometimes referred to separately, the difference between them only is that in method A using an N,N-dialkyl aromatic amine which becomes substitued in the aromatic ring in para- or ortho position, a chloro atom becomes attached to an unsaturated aromatic carbon atom, while in method B a chloro atom is introduced in saturated allylic position According to British Pat. No. 1,467,610, it is in view of the occasionally good yields indicated therein, however without being corrected for the actual contents of the finally isolated products, also somewhat more generally possible to employ a tertiary amine like pyridine which is not substituted with chlorine during the deoxygenation but may conceivably incapacitate chlorine to some extent by formation of molecular complexes between the amine and molecular chlorine.

In connection with some remarks relating to possible reaction mechanisms, method A has been indicated by Wakisaka et al [Synthesis, p. p. 67–68 (1980)]. As referred to already above, the use of dimethylaniline and other, preferably weak, tertiary amines like pyridine is described in British Pat. No. 1,467,610 whereby as alleged therein, good yields were also obtained in two-step one-pot synthesis of 7β-amino-3-substituted methyl-3-cephem-4-carboxylic acid derivatives starting from corresponding 7β-acylamino-3-substituted methyl-3-cephem-4-carboxylic acid-1β-oxide derivatives even when using "silicium" esters of the starting materials.

Method B, using enamines such as 1-morpholino-1-cyclohexene and phosphorus pentachloride, in the mean time has become a standard method for the deoxygenation of cephalosporin-1-oxides and this method has been described by Wakisaka et al (same reference), indicating in addition that in the general sense enamines are more effective than dialkylanilines for the capture of chlorine because of lesser participation of side reactions.

Since the combined prior art of these interrelated methods pointed at possibly rewarding application even in the case of using "silicium" esters, methods A and B were considered to be the most eligible candidates for the development of the two-step, and in particular of the multi-step one-pot process of the present invention. Indeed, in single step experimentation comprising the use of silylated intermediates, deoxygenation in the presence of such an amine proved to be well useful, particularly when using relatively stable substrates like phenylacetamido-desacetoxycephalosporin-1β-oxide, whereby dimethyl aniline behaved superior to 1-morpholino-cyclohexene in that optimum yields of over 90% were obtained at −45° C. in appreciably shorter time. The capture of chlorine by such agents was still substantially effective, but definitely already to smaller extent, when the substrate comprised a heterocyclic thiomethyl group as a substituent in position 3. Surprisingly, however, it was found that the yields of conversion and the true yields of isolation went down to a barely interesting level upon combination of this deoxygenation process with the last step to give the final 7β-amino-3-cephem-4-carboxylic acids, although application of extended reaction times during the deoxygenation and/or of a greater excess of reagents somewhat improved this picture. In cases of using and introducing such more intricate and more interesting substituents in position 3, combination of the deoxygenation step comprising phosphorus pentachloride and such amines or enamines with the preceding steps in multi-step one-pot synthesis, all aspects viewed together, appeared not interesting enough so that in particular a complete sequence without isolation of any intermediate could not be performed on an economically attractive basis, particularly when using silylated intermediates.

Henceforth, it became a primary object of this invention to develop a new deoxygenation process which under practical conditions had to be at least as efficient as any of the known cephalosporin-1-oxide deoxygenation processes in single step experimentation, while using in particular "silicium" esters of not only relatively stable desacetoxy-cephalosporin-1β-oxides but also of cephalosporin-1β-oxides having a more intricate substitution pattern at position 3 of the cephem nucleus, in the hope that the conditions of the new process would turn out to be appropriate for accommodation in multi-step one-pot syntheses.

Since the primary basic agent in the deoxygenation, phosphorus pentachloride, remained to be interesting, it was contemplated whether another type of secondary agent in its capacity to capture chlorine preferably operating by a substantially different mechanism could be more effective especially with regard to use in multi-step synthesis and to the use of silylated intermediates. Secondary agents like pyridine under the conditions involved conceivably take up chlorine merely by complexation, while agents like a dialkyl-aniline or a classic enamine, apart from possible initial incapacitation of chlorine by complexation, react with chlorine only by substitution of hydrogen by forming one carbon-chlorine bond for each molecule of chlorine consumed. The capture of chlorine during this type of deoxygenation reaction by addition to a suitable carbon-carbon double bond with formation of two carbon-chlorine bonds per molecule of chlorine consumed apparently was either not considered or found not to be effective, which to certain degree may seem surprising, since the reaction, i.e. addition and/or substitution, of chlorine with simple non-enamic olefins is a well-known and much practiced conversion as can be deduced from the prevailing enormous amount of literature.

However, just the fact that there is such an enormous amount of literature on this seemingly simple reaction is an indication that this matter still is not sufficiently understood comprehensively as is evident from the contents of the many reviews on this topic. The intrinsically complex state of affairs is expressed coherently by for instance Sharma et al in "Halogenation of Olefins" [Indian Chemical Manufacturer,Vol. 12 (No. 6), p.p. 25–35 (1974)]. Apparently, the velocity of the conversion, the main course of the conversion, i.e. addition and/or substitution, the extent of catalysis possible, the influence of light and oxygen, the influence and the participation in end products of solvents used, etc., are in a still not understandable way determined by various factors such as the structure of the olefin so that it is very well possible that attempts made elsewhere failed to give attractive results in spite of using apparently appropriate conditions, just as an attempt with a perfectly normal olefin like cyclohexene failed to give a promising result in an earlier phase of the investigations leading to the development of the multi-step processes of this invention.

Although the successful addition of bromine to simple olefin during deoxygenation of "carbon" esters of cephalosporin -1-oxides is known from the U.S. Pat. No. 4,044,002, it will be appreciated that this patent lacks sufficient antecedent basis in this connection since in view of other aspects, the processe are not substantially the same as the addition of bromine in said process takes place at an appreciably higher temperature range, the possibility of using "silicium" esters in said process is not taught and the reaction of bromine with the carbon-carbon double bond is according to the vast literature an appreciably less problematic event.

Since a preliminary attempt involving non-catalysing con ditions and a common olefin, i.e., cyclohexene, as used on trimethylsilyl 7$\beta$-phenylacetamido-3-(1-methyl-(1H)-tetrazol-5-yl-thiomethyl)-3-cephem-4-carboxylate-1$\beta$-oxide prepared by silylation with hexamethyl disilazane, produced a disappointing result, it was tried whether a somewhat unusual olefin, i.e. cis-cyclooctene, when used on a more stable substrate could perform better.

In single step experimentation, the results of using small excesses of phosphorus pentachloride and ciscyclooctene on trimethylsilyl esters of the 1$\beta$-oxides of 7$\beta$-phenylacetamido-3-methyl-3-cephem-4-carboxylic acid (a relatively stable substrate) and of 7$\beta$-phenylacetamido-3-(1-methyl-(1H)-tetrazol-5-yl-thiomethyl)-3-cephem-4-carboxylic acid (a relatively vulnerable substrate), prepared in situ in dichloromethane with the help or varying but mutually equal excesses of trimethyl chlorosilane an N,N-dimethyl aniline, were quite surprising. When accounting for the actual contents of the starting and final products, the true yields of conversion and isolation obtained after 15 minutes of reaction at $-45°$ C. were excellent and exceeded those reached by any other known deoxygenation process tried out.

It will be appreciated that under the hereinabove indicated conditions constituting only one operational method of the present deoxygenation process, part of the chlorine is concomitantly consumed by substitution of N,N-dimethyl-aniline to a relative degree varying with the size of the excess of this agent as it is introduced to effect fast and diligent silylation of the substrate cephalosporanic acid-1-oxides so that in a certain way this successful operational method then combines two chlorine consuming secondary agents, one of which, i.e. N,N-dimethylaniline, was known to be effective though not under identical conditions. In this respect it is to be inferred however, that in contrast with prior art procedures, the dimethyl-aniline in this modification of the present deoxygenation process is used in conjunction with an at least substantially equal excess of the chlorosilane agent.

Further extensive practical investigation of the true nature of the present deoxygenation process revealed various important features to be taken into account in order to arrive at a number of advantageous operational procedures of the versatile new deoxygenation process of the present invention.

It appeared that the initial disappointing result of cyclohexene under the conditions indicated was not so much caused by the relatively vulnerable nature of the particular substrate used, nor by the circumstance that under identical conditions, which are not accommodated specifically to the individual nature of this olefin, cyclohexene usually is less effective than cis-cyclooctene, which particular olefin for presently not explainable reasons proved to be more effective than most other olefinic compounds containing an ethylenic bond with a total of two or three hydrogen atoms attached to the unsaturated carbon atoms.

When using "carbon" esters of cephalosporanic-1-oxides, the need for catalysis appeared to be not so prominent, and in such cases catalysis even can be deleted occasionally. However when using "silicium" esters, catalysis appeared to be almost a necessity, at least when the conversions are aimed at the same lower temperature and short reaction times.

It is well known from the general art that the reaction of molecular chlorine with the olefinic double bond can be catalyzed in various ways. However, the matter has appeared to be extremely complex as it involves variation with the particular nature of the double bond and with furth;r conditions like the constitution of the reaction medium. Product consitution may also be effected by catalysis. Somewhat similarly, particularly relating to complexity of the phenomcnon, the capture of chlorine by the secondary agents of olefinic nature used in the present deoxygenation process also can be catalyzed in various ways.

A clear-cut case of catalysis was found when using as catalyst N,N-di(lower)alkylformamide such as N,N-dimethylformamide, of which a relative amount of up to 30 mol percent with respect to the amount of cephalosporin introduced appeared to be sufficient usually. This type of catalyst can be used advantageous particularly when starting with separately prepared, more or less pure esters, or from in situ prepared esters or anhydrides, when such preparations do not involve excesses of catalysing agents as is the case with trimethylsilylation with hexamethyl disilazane as described in European patent application No. 0043,630, which is included herein by reference, or when reaction by-products resulting from the ester preparation method do not constitute catalyzing substances themselves.

In about the same relative amounts as indicated hereinabove, some types of tertiary amines in such cases also provide for efficient catalysis, whether or not at the same time combined with an at least equivalent amount of an acidic, conceivably complexating compound, such as e.g. trimethyl chlorosilane and very suitable amines in this respect are N,N-dialkyl-anilines. Thus, simultaneous introduction of about 10 mole percent of N,N-dimethyl-aniline to a deoxygenation of a cephaloporanic acid-1-oxide trimethylsilyl ester prepared with hexamethyldisilazane produces a significant catalytic effect which cannot be explained solely by the circumstance that a small part of the chlorine is consumed by nuclear substitution of this amine.

While some other types of tertiary amines, whether or nor prone to substitution by chlorine, similarly exert a catalytic influence, some tertiary amines which are virtually not substituted by chlorine during the conversion may even significantly retard the deoxygenation. Meant herewith are pyridine and some pyridine type amines which appear to form strong molecular complexes with phosphorus pentachloride, apparently even when used in conjunction with an equivalent amount of e.g. trimethyl chlorosilane. The experimental observations involved are in acute contradistinction with the process of British Pat. No. 1,467,610 wherein pyridine and N,N-dimethyl-aniline are named in one breath.

Generally, hydrochloric acid salts of various tertiary amines may also provide for catalysis to some extent and such salts are generated automatically upon dissolving the starting 1-oxides of cephalosporanic acids with a halogen containing agent and a tertiary amine. Various tertiary amines, like the relatively strong basic aliphatic tertiary amines, e.g. triethylamine, therefore can be used in this respect, but when using some pyridine-type bases, introduction of significant excesses of such bases were found to be avoided in the context of fast deoxygenatiohs at relatively low temperatures in view of retardation caused by the formation of complexes between e.g. pyridine and phosphorus pentachloride even when the excess of such a base is compensated for by an at least equivalent excess of the halogen-containing esterification agent, e.g. trimethyl chlorosilane.

Another feature to be considered to arrive at suitable use of the present deoxygenation process relates to an aspect well-known in the art. Several types of olefinic compounds and a number of individual olefinic compounds, even when able to consume molecular chlorine at a fast rate at relatively low temperature, do this not only by addition to the carbon-carbon double bond, but at the same time also by substitution at e.g. one unsaturate carbon atom or an adjacent carbon atom, so that hydrochloric acid is formed simultaneously. This matter has appeared to be extremely complex and the ratio betwen addition and substitution is dependent on the reaction conditions selected for instance.

Referring to olefinic compounds of relatively simple structure, 1-olefins like 1-hexene having three hydrogen atoms attached to the two unsaturated carbon atoms, may depending on the further conditions take up molecular chlorine to a significant degree by substitution. The relative extent of substitution may be reduced considerably when using at the same time the generally much faster reacting 1-olefins having no hydrogen atom attached to the non-terminal unsaturated carbon atom, while it often is negligible when employing olefinic compounds with nonterminal carbon-carbon double bonds, like 2-hexene, etc.

When using silyl groups for the protection of the 4-carboxylic acid groups, which groups are vulnerable by themselves and/or make the whole molecule more sensitive, this aspect was somewhat similarly experienced in the present process, notwithstanding that the process at least at low temperatures probably does not involve a reaction with free molecular chlorine.

In those cases, the use of 1-olefins like 1-hexene is accompanied by introduction of a less than equivalent amount of a suitable tertiary amine like triethyl amine, but not pyridine to combat adverse effects displayed by presumably hydrochlroic acid developed during the reaction. It is then generally sufficient to use about 50 mol percent of the base, or a smaller amount if the relative extent of sustitution of the olefin can approximated by experimentation or by information derivable from the art. The base can be introduced at once at the beginning or the deoxygenation, or gradually during this conversion. It is noted hereby, that an excess of tertiary amine base eventually employed in the preceding esterification step may not be adequate in view of too large overall acidity of the medium as a consequence of using that excess in conjunction with an at least equally excessive amount of the halogen containing agent, e.g. trimethyl chlorosilane.

It will be appreciated that the use of such olefins like 1-hexene, which as indicated above involves the use of selected conditions adjusted individually and which in addition requires relatively more extended reaction times and/or higher temperatures, is generally not preferred when the deoxygenation reaction of the invention is incorporated in the one-pot multi-step processes of the invention in view of eventual measures to accommodate the deoxygenation step to other steps therein, particularly when such processes are associated with protective silylation.

Accordingly it was found that, at least in single step experimentation, olefins varying widely in the nature of the carbon-carbon double bond can be used as secondary agents in the phosphorus pentachloride mediated deoxygenation of esters of various cephalosporanic acids-1-oxides, and that the suitability of an arbitrary olefin is related to finding individually appropriate conditions with regard to e.g. the nature of the esterifying group, to catalysis, and to the extent of competing substitution of the olefin instead of selective addition to the carbon-carbon double bond.

The first object of the present invention therefore relates to a single step process for the deoxygenation of cephalo-sporin-1β- and/or cephalosporin-1α-oxides of the formula

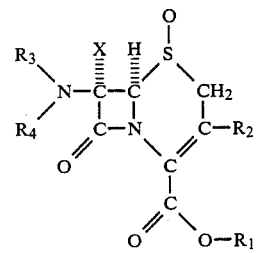

by reaction with phosphorus pentachloride into correspondingly substituted cephalosporines of the formula

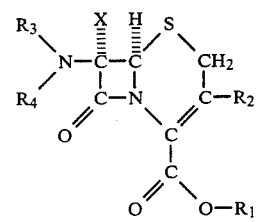

optionally followed by removal of the protective group R to give the compounds of formula II wherein $R_1$ is hydrogen or a salt forming cation and/or of groups introduced optionally to protect reactive groups present in the substituent $R_2$ and $R_3$ wherein X is hydrogen, (lower) alkyloxy or (lower)alkylthio, lower alkyl throughout indicating 1 to 4 carbon atoms, $R_1$ is a protective group as commonly used in cephalosporin chemistry such as a silyl group like trimethylsilyl, dimethyl chlorosilyl and dimethyl silyl via carboxylate oxygen attached to an additional cephalosporanyl moiety of formula I, t-butyl, pentachlorophenyl, 2,2,2-trichloroethyl, benzhydryl or benzyl like 4-nitro-benzyl, and 4-methoxybenzyl, $R_2$ is a highly variable atom or group comprising; hydrogen or chlorine, methoxy, trifluoromethyl, vinyl, methyl, and methyl substituted by halogen such as chlorine or bromine, protected hydroxy like trialkylsilyloxy, (lower)alkyloxy, (lower)alkylthio (lower)alkanoyloxy like acetoxy, (lower)alkanoylthio, 1-pyridinium optionally having substituents attached to the heterocyclic ring, or a heterocyclic thio group optionally substituted in the heterocyclic ring, wherein the heterocyclic radical can be pyridine, pyrimidine, pyridazine, pyrrole, imidazole, pyrazole, isoxazole, oxazole, isothiazole, thiazole, 1,2,3-(lH)-triazole 1,2,4-triazole, 1,2,4- and 1,3,4-oxadiazole, 1,2,4-, 1,3,4-, 1,2,3- and 1,2,5-thiadiazole, 1,2,3,4-thiatriazole and (lH) tetrazole linked by a ring carbon atom to the sulfur atom, the optional substituents attached to a ring carbon atom of a heterocyclic ring include optionally substituted lower alkyl, cyano, chloro, di(lower)alkylamino, (lower)alkyloxy like methoxy, (lower)alkyloxycarbonyl, di(lower)alkylcarbamoyl, hydroxy, sulfo and carboxy, while ring nitrogen atoms of the heterocyclic thio group can have attached thereto an optionally substituted lower alkyl group, and optional substituents attached to the first or the second carbon atom of a lower alkyl group attached to a carbon or a nitrogen atom of a heterocyclic ring may include di(lower)-alkylamino, chloro, cyano, methoxy, (lower)-alkoxycarbonyl, N,N-dimethyl-carbamoyl, hydroxy, carboxy and sulfo, optionally implicating precedingly or in situ adjusted protection of hydroxy, carboxy, sulfo and heterocyclic secondary amino groups by silylation or in the last case optionally also by acylation.

$R_3$ is a highly variable acyl such as formyl, alkanoyl, alkenoyl, aroyl, heterocyclic carbonyl, aryloxyacetyl, cyanoacetyl, haloacetyl, phenylacetyl, α-hydroxy-, α-carboxy and α-sulfo-phenylacetyl, α-carboxy-thienylacetyl, α-acylamino-phenyacetyl, α-(substituted)oxyimino-aryl(or - furyl, or -thiazolyl) acetyl, optionally having attached to an aromatic or heterocyclic ring substituents including chlorine, fluorine, methoxy, cyano, lower alkyl, hydroxy and carboxy, optionally implicating easily removable protection of reactive substituents introduced in advance or in situ by silylation or by acylation in the case of a secondary amino group placed in an unsaturated ring, or $R_3$ forms together with $R_4$ and the nitrogen atom phthalimido and $R_4$ is hydrogen except when $R_4$ is incorporated in phthalimido.

According to the invention, such a single step process for the deoxygenation of generally cephalosporin-1-oxides by reaction with phosphorus pentachloride is thereby characterized, that the deoxygenation is carried out at −70° to 0° C. in a substantially inert organic solvent in the presence of in any case an olefinic compound having at least one carbon-carbon double bond with no more than three hydrogen atoms attached thereto, the olefinic compound having the function of removing chlorine at least in part by addition to a carbon-carbon double bond. Enamines like 1-morpholino-1-cyclohexene are excluded from the invention since from the prior art they are known to be effective in this respect.

Basically, instead of phosphorus pentachloride, alternative agents known in the prior art to be effective in the deoxygenation of sulfoxides like phosphorus pentabromide can be used more or less generally, but phosphorus pentachloride clearly is the industrially preferred agent.

Since the ability of olefins to remove chlorine from the phosphorus pentachloride mediated deoxygenation of cephalosporin -1-oxides was found to parallel very much the ability of olefins to take up molecular chlorine at least in part by addition to the carbon-carbon double bond, in principle any olefin that can take up molecular chlorine under similar conditions in a fast reaction below 0° C. can be used in the process of this first object of the invention.

Consequently, the olefinic compound can be a monoolefin, a diolefin, or polyolefin with one or more carbon-carbon double bonds placed in a chain or in a ring. If the olefinic compound contains more than one carbon-carbon double bond the relative amount of olefin used can be reduced according to the number of double bonds. In a diolefin or polyolefin, the double bonds can be in conjugated or in not conjugated position, though clearly excluding benzenoid compounds and heteroaromatic compounds which do not add chlorine easily to carbon-carbon double bonds.

In view of environmental considerations, a polyolefinic compound can also be a polymeric compound with carbon-carbon double bonds more or less regularly attached to a support frame, particularly when using silyl protection of the cephem-4-carboxylic acids. It is also possible to employ α, β-unsaturated functional compounds such as α, β-unsaturated nitriles, though then preferably with no more than one hydrogen atom attached to each carbon atom of the carbon-carbon double bond.

The olefinic compound can have various substituents in various positions, but there is no sense in having a highly electronegative group like nitro attached to one of the unsaturated carbon atoms or to an adjacent carbon atom in view of considerable reduction of the electron density at the unsaturated center. Less compatible also are substituents like hydroxy, carboxy and carbamoyl which may interact with phosphorus pentachloride. Possible substituents placed at adjacent or further removed positions are for instance alkoxy, alkylthio, bromine, or chlorine, chlorine being already introduced automatically if a diolefin is used in about half equimolar amounts.

Particularly in view of extra costs usually associated with the use of polyolefins and intricately substituted olefinic compounds, a set of primarily suitable olefinic compounds comprises monoolefins and diolefins having one or both carbon-carbon double bonds placed in a chain of 3 to 20 carbon atoms or in a ring of 4 to 12 ring carbon atoms, whereby the total number of hydrogen atoms attached to the carbon atoms of a carbon-carbon double bond is not greater than two, comprising non-terminal carbon-carbon double bonds and terminal ones having no hydrogen atoms attached to the inner unsaturated carbon atom.

Although it is normally and in view of the prevailing conditions in this process not easily possible to predict accurately the extent of addition of chlorine over the extent of substitution by chlorine, it is in general and in particular in the case of the use of "silicium" esters of the cephalosporanic acid-1-oxides more preferred to use a monoolefinic or diolefinic compound having one or two non-terminal carbon-carbon double bonds since it can be deduced from the prior art that generally the extent of substitution is increased by placing the double bond in terminal position. The olefinic compounds comprised may exhibit cis-trans isomerism, but there is often no preference or only little advantage in using the trans isomer instead of the corresponding cis isomer and vice versa.

In accordance with a well-known aspect that trisubstituted olefinic bonds and even more tetrasubstituted olefinic bonds take up molecular chlorine appreciably faster than non-terminal disubstituted olefinic bonds, quite suitable olefins in the process of the invention are those olefinic compounds which contain one or two non-terminal carbon-carbon double bonds whereby one or both carbon atoms of the double bond are additionally substituted by straight lower alkyl of 1 to 4 carbon atoms.

A generally very effective and with respect to other olefins having a non-terminal disubstituted double bond somewhat preferred olefin appeared to be cis-cyclooctene. The somewhat preferred position of this olefin with respect to similar olefins like cycloheptene and hexene-2 is not so much related to better yields of conversion obtained therewith, since the difference in this regard often is only small. However, it was found surprisingly that starting from various substrates of formula I, it was often easier to reach with cis-cyclooctene in a few attempts a very satisfactory yield of isolation as well. Using cis-cyclooctene under practical conditions, it appeared to be no longer necessary soon to treat mother liquors to arrive at yields of isolation close to yields of conversion as determined by high pressure liquid chromatography.

A generally suitable range for the temperature during the deoxygenation apoeared to be −60° to −20° C. and the choice of the temperature is largely determined by the structure of the olefin selected and by the stability of the protecting group $R_1$, the nature of which also appeared to influence the reactivity of the sulfoxy group towards deoxygenation. If $R_1$ is a vulnerable group like trimethylsilyl, it is generally advantageous to use temperatures below −30° C., whereby it makes a difference how precisely the "silicium" ester is prepared in situ. If such an ester is prepared with about equal excesses of a chlorosilane agent and of a suitable tertiary amine like triethylamine or dimethylaniline, it is advisable to use temperatures of about −40° C. to exclude completely the possibility of some additional splitting of the 7β-acylamino substituent by the small excess of phosphorus pentachloride normally introduced for the deoxygenation. The danger herefore is in practice anyhow minimal since according to the silylation method used in the process of the invention, the excess of base introduced during silylation is alwavs compensated for by an at least substantially equivalent amount of chlorosilane agent.

The deoxygenation of the invention is carried out in a substantially inert organic solvent. In this respect, various types of solvents can be used, for instance ether type and alkyl ester type solvents. Good yields and little accommodation to to the nature of the solvent result from the use of alkyl nitriles like acetonitrile and propionitrile. Particularly good solvents are halogenated hydrocarbons like chloroform, dichloromethane and 1,2-dichloroethane. If desired for reasons of e.g. solubility of the esters of formula I, solvents of different kinds can be combined.

As indicated before, the deoxygenation process of the invention is qenerally more suitably carried out in the presence of a catalyst or an additive promoting fast conversions at relatively low temperature. As explained, rapid conversion promoting substances can already be present when the protective esterifying group $R_1$ is introduced, preferably in situ, by reacting the starting cephalosporanic acid-1-oxide with e.g. a halogen containing agent like trimethylchlorosilane in the presence of a suitable tertiary amine.

Generally, and particularly when starting from previously prepared more or less pure "carbon" esters or from other types of esters or anhydrides, preferably prepared in situ, with agents which do not provide for catalysis in the subsequent deoxygenation by themselves or by the products of their conversion in the esterification or anhydride forming procedure, such as e.g. hydro-chloric salts of a tertiary amine, a catalyst or conversion promoting agent is introduced deliberately. Preferably, such a deliberately added catalyst or conversion promoting substance is economically used in relative amounts not exceeding 30 mole percent with respect to the quantity of the cephalosporin-1-oxide used.

Preferred compounds in this respect are N,N-di(lower)alkyl-formamides such as N,N-dimethyl-formamide, and/or generally tertiary amines which conceivably do not engage in relatively strong complexes with phosphorus pentachloride and which may or may not consume by substitution part of the chlorine removable from the deoxygenation reaction. Preferred tertiary amines in this respect are the N,N-di(lower)alkyl-anilines like N,N-dimethyl-aniline.

In view of the before indicated aspect, that an arbitrary olefinic compound used as secondary agent in the deoxygenation process of the invention to varying relative extent may not consume chlorine solely by addition to a carbon-carbon double bond, the deoxygenation conditions can be complemented by simultaneous or gradual introduction of maximally 50 mol percent of a relatively strongly basic tertiary aliphatic amine like triethylamine or N-methyl-morpholine or the like, to neutralize the hydrochloric acid developed. If the extent of catalysis provided by this base and/or by its hydrochloric acid salt is not sufficient for a fast conversion at low temperature, a few mole percent of an N,N-di(lower)alkylformamide is introduced as well.

The starting compounds of formula I for the process of the first object of the invention possess a protective group $R_1$ which imparts to these compounds the character of either a mixed anhydride or an ester.

The mixed anhydrides of formula I generally are prepared preferably in situ and the protective group is removed after the deoxygenation by mild hydrolysis, preferentially carried out in situ, to give the compounds of formula II with $R_1$ as hydrogen or a salt forming cation. Agents for the preparation of the mixed anhydride type of compounds of formula I can be carboxylic acid halides like acetyl chloride, chloroacetyl chloride, benzoyl chloride, or chloroformates like methyl- and ethyl chloroformate, compounds containing one or more phosphor-halogen bonds like phosphorus pentachloride, phosphorus oxytrichloride, phosphorus trichloride, methoxy dichlorophosphine, 2-chloro-1,2,3-dioxaphospholane-, 5-methyl-2-chloro-1,2,3-dioxaphospholane, ethoxy dichloro-phosphate, methoxy dibromophosphate, or preferably compounds containing one or more silicium-halogen bonds like methoxy trichlorosilane, methyl dimethoxychlorosilane, methyl methoxydichlorosilane, diphenyl dichlorosilane, dimethyl t-butylchlorosilane, triethyl chlorosilane, dimethyl methoxychlorosilane, dimethyl dichlorosilane and as particularly preferred, trimethyl chlorosilane.

If the agent contains two or more reactive halogen atoms, the resulting compounds of formula I may still contain one or more halogen atoms linked to a central atom, e.g. silicium or phosphor, and/or may contain two or more cephalosporanyl moieties linked through carboxylate oxygen with the central atom, e.g. silicium or phosphor. Silyl groups substituted with lower alkyl groups like methyl and ethyl and/or with lower alkoxy groups like methoxy and ethoxy can also be introduced with the help of the correspondingly substituted disilylamines (disilazanes).

The "carbon" esters of formula I usually are prepared by a separate preceding step using in one way or the other, various hydroxy carbon compounds. After the deoxygenation, the compounds of formula II still containing the protective group $R_1$ are isolated as such or are subjected to hydrolytic or reductive methods known per se to give the compounds of formula II wherein $R_1$ is hydrogen or a salt forming cation. The hydroxy carbon compounds from which esters of formula I are derived are pentachlorophenol, 2-chloro and 2-bromo ethanol, 2-methyl and 2-ethyl-sulfonylmethanol, triphenylmethanol, benzoylmethanol, 4-bromobenzoylmethanol, trimethylacetyloxymethanol, acetoxymethanol, 5-hydroxy -5-methyl-tetrahydrofurane-1-one, 3-hydroxy-3-methyl-1,3-dihydro isobenzofurane-1-one and similar compounds used in the chemistry of cephalosporins. Preferably the hydroxy carbon compounds are are pentachlorophenol, 2,2,2-trichloroethanol, diphenylmethanol, benzylalcohol, 4-nitro and 4-methoxy benzylalcohol and t-butanol If the carbon esters of formula I to be employed in the deoxygenation contain secondary substituents in need of protection eventually like hydroxy, carboxy and sulfo groups attached to substituents $R_2$ and $R_3$, protection suitably is carried out in situ preceding deoxygenation, preferably by silylation using either e.g. trimethylchlorosilane and a suitable tertiary amine like triethylamine, N,N-dimethyl-aniline, or e.g. hexamethyldisilazane and a catalyst like saccharine. Secondary unsaturated heterocyclic amine groups such as present in imidazole and 1,2,3-(1H)-triazole likewise can be protected by silylation or by acylation with the help of a simple acid chloride like acetyl chloride or benzoyl chloride or a lower alkyl chloroformate in view of easy removal of such acyl groups by mild hydrolysis afterwards.

If carboxylic acids or carboxylate salts of formula I are to be employed as starting materials, protection of the ceohalosporin 4-carboxylic acid group is preferably carried out in situ by forming a mixed anhydride. If such starting cephalosporanic acid-1-oxides also contain one or more of the above-mentioned reactive secondary substituents, protection of all substituents in need of protection is introduced preferably by silylation, optionally combined with acylation of the kind of secondary heterocyclic amine groups indicated above. In practice however, such additional protection of reactive substituents contained in $R_2$ and $R_3$ is often not necessary.

The experimental manipulation of the process of the first object of the present invention is simple. The solution of an ester or a mixed anhydride of formula I in a suitable solvent system, eventually after preceding preparation in situ of a mixed anhydride and protection of reactive secondary substituents by e.g. silylation, is brought to the selected reaction temperature or to an initially somewhat lower temperature. Optionally during cooling or after reaching the selected low temperature, the olefinic compound is added in preferentially 0–30% molar excess if this compound is a monoolefin. If the olefinic compound contains more than one carbon-carbon double bond, the relative molar amount of the olefinic compound optionally can be reduced substantially in relation to the number of double bonds while maintaining an excess equivalent of 0–30%.

Ignoring possibly somewhat exceptional cases, the general conditions for using or not necessarily using catalysts or rapid conversion promoting substances are as follows:

As indicated before, preferably 0–30 mol % of a suitable catalyst is optionally introduced if the starting compound of formula I is an ester or a mixed anhydride derived from a cephalosporanic acid-1-oxide and e.g. a carboxylic acid. Though somewhat depending on the nature of the olefinic compound, introduction of a catalyst usually is necessary when using as starting materials other types of mixed anhydrides, in particular referring to "silicium" esters, when such mixed anhydrides were not prepared in situ by a combined agent leaving unused amounts of the combined agent and/or reaction products like HCl salts of suitable tertiary amines. If the selected olefinic compound reacts with chlorinating species substantially not only by addition of chlorine, about 50 mol % or less of a suitable tertiary amine like triethylamine is now introduced at once or gradually together with a few mole percent of an N,N-di(lower)alkylformamide, if necessary.

In a few cases wherein the nature of the substituent $R_2$ in practice exerts a relatively elevated negative effect on the reactivity of the sulfoxy group, e.g. when $R_2$ is 1-pyridiniummethyl, the use of a catalytic amount of e.g. N,N-dimethylformamide can be advantageous in any operational procedure of the deoxygenation process of the invention.

About 5–30% molar excess of phosphorus pentachloride is introduced subsequently followed by a stirring period at the selected low temperature, the extent of which depends mainly on the chosen reaction temperature. By way of indication, even when employing suitably prepared "silicium" esters, about 15 minutes additional stirring at −45° C. usually is long enough. The reaction mixtures obtained are carefully hydrolyzed in the usual way.

In view of the difficulties experienced with the combination in one pot of even the best and most appropriate prior art cephalosporin-1-oxide deoxygenation processes with other steps envisaged, it certainly could not be expected by one skilled in the art that the present deoxygenation process, in spite of good and even superior behavior in single step experimentation, indeed could be inserted satisfactorily and without undue accommodation in two-step and multi-step one pot processes.

Therefore, the seemingly easiest combination, that is a two-step one pot process comprising the new deoxygenation process of the invention and the splitting of the 7β-acylamino substituent preferentially involving as agent phosphorus pentachloride by methods substantially known per se in the prior art, was tried out first. Surprisingly, the need for accommodation fortunately was slight in practice so that the new deoxygenation process was amenable to one pot conversions with at least a substantial part of the compounds comprised by formula I to give the correspondingly substituted 7β-amino-cephalosporanic acid derivatives at positions 3 and 7.

Accordingly, the second object of the invention relates to a process for the synthesis of 75-amino-cephalosporanic acid derivatives of the formula

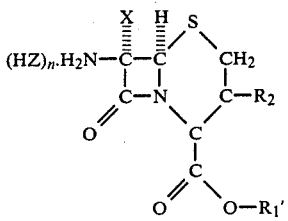

III optionally comprising removal of "carbon" ester residues $R_1'$ to give compounds of formula III wherein $R_1'$ is hydrogen or a salt forming cation wherein X is as defined above $R_1'$ is hydrogen or a salt forming cation or a "carbon" ester residue like pentachlorophenyl, benzyl, 4-nitro-benzyl, 4-methoxy-benzyl, benzhydryl, 2,2,2-trichloroethyl and t-butyl, $R_2$ is as defined above, but implicating that precedingly introduced silyl groups to protect hydroxy, carboxy and sulfo groups and/or silyl groups or acyl groups to protect unsaturated heterocyclic secondary amine groups are removed to give the free substituent or salts thereof, HZ is a salt forming strong acid like p-tolyl-sulfonic acid or hydrochloric acid as commonly used in cephalosporin chemistry, and n is ad libitum 0 or 1 when X is hydrogen and when X is not hydrogen combined with $R_1'$ is hydrogen, or n is 1 when X is not hydrogen and $R_1'$ is a "carbon" ester residue.

According to aspects well known in cephalosporin chemistry, the isolation of the compounds of formula III in the form of acid addition salts, hereinabove denoted by $(HZ)_n$, primarily is a matter of convenience in the isolation procedure and of stability. Irrespective of the nature of the group $R_1'$, n can be ad libitum zero or 1 if X is hydrogen. If then $R_1'$ is hydrogen, n normally is zero, while when $R_1'$ is a carbon ester residue like t-butyl, it can be convenient to isolate the compound as the acid addition salt (n=1). If however X is not hydrogen, stability of the final product may necessiate isolation as acid addition salt in following methods known per se, particularly when at the same time $R_1'$ is a carbon ester residue. As is known also, the matter of forming acid addition salts is at variance to formation of internal salts due to the presence of additional carboxy, sulfo, unsaturated heterocyclic secondary amino groups and tertiary dialkylamino groups in the substituent $R_2$ and to cases wherein $R_2$ is a 1-pyridinum-methyl group.

According to the second object of the invention, such a two-step process for the preparation of compounds of the formula III is thereby characterized in that 7β-acylamino-3-cephem-4-carboxylic acid-1-oxide derivatives of the formula

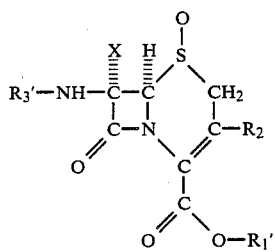

Ia wherein X is as defined above, $R_1'$ is hydrogen or a salt forming cation or a "carbon" ester residue as defined above, $R_2$ is as defined before, implicating protection of reactive substituents contained in $R_2$ prior to deoxygenation as described above, and $R_3'$ is a substituted acetyl group $R_5$—$CH_2$—CO similar to a group which can be introduced by penicillin fermentation, and wherein $R_5$ is hydrogen, aryl, alkyl, cycloalkyl, alkenyl, aryloxy, alkyloxy, arylthio, alkylthio, or $R_3'$ is benzoyl, are converted without isolation of the product of deoxygenation by sequentially the following steps, optionally performed in the same reaction vessel:

(a) a silylation of the cephalosporin-4-carboxyl group when starting from compounds of formula Ia wherein $R_1'$ is hydrogen or salt forming cation, and/or an optional protection by silylation and/or acylation of reactive substituents contained in $R_2$ as described above, (b) a deoxygenation in a halogenated hydrocarbon solvent employing phosphorus pentachloride in the presence of in any case an olefinic compound having at least one carbon-carbon double bond with no more than two hydrogen atoms attached thereto which removes chlorine predominantly by way of addition to carbon-carbon double bond, and optionally in the presence of added or already present catalyst or additive, (c) a deacylation reaction splitting the 7β-acylamino substituent by known procedures by adding sequentially a suitable tertiay amine like dimethyl aniline and phosphorus pentachloride to form in situ the correspondence imide chloride, and a suitable monohydroxy alkane like isobutanol or an alkanediol like 1,3-dihydroxy-propane to form the corresponding imino ether and finally water for hydrolysis of the imino ether group and of easily removable protective groups.

It is experimentally possible to carry out the active sequence of steps in one and the same reaction vessel up to the final hydrolysis which for at least a part also can be performed in the same vessel. It is occasionally advantageous to add the imide chloride containing reaction mixture of step (c) to the excess of precooled hydroxy alkane placed in a second vessel. The final products of formula III are isolated by methods basically known per se optionally including hydrolytic or reductive fission of a carbon ester residue $R_1'$.

While other types of solvents can be used occasionally in the process of the second object of the invention, it is generally preferred to employ halogenated hydrocarbons like chloroform, 1,2-dichloroethane and in particular dichloromethane. In view of also the generally suitable temperature below −35° C. for the phosphorus pentachloride mediated imide chloride forming step (c), it is preferred to carry out the deoxygenation step (b) at temperature between −35° and −65° C. to minimize extra costs associated with additional cooling.

For reasons of economy particularly and in view of most appropriate accommodation to the subsequent amide bond fission, it is preferred to carry out the deoxygenation with phosphorus pentachloride in the presence of a monoolefinic compound having non-terminal carbon-carbon double bond placed in a chain of 4 to 12 carbon atoms optionally substituted on one or at both unsaturated carbon atoms with a methyl or ether group or in a carbocyclic ring of 5 to 8 ring atoms optionally substituted at one unsaturated carbon atom with a methyl or ethyl group. In view of expedient isolation of the final products in isolation yields closely approaching yields of conversion, a singularly effective olefin appeared to be cis-cyclooctene.

In using the starting compounds of formual Ia, the generally preferred protective group $R_1'$ is trimethylsilyl. When using "carbon" esters of formula Ia, the t-butyl group is somewhat preferred over other similar groups $R_1'$. The groups $R_3'$ preferably used are phenylacetyl and phenoxyacetyl.

A third object of the present invention is a multi-step synthesis up to the final isolation procedure preferably carried out in one and the same reaction vessel, of 7β-acylamino-cephalo-sporanic acid derivatives starting from 7β-acylamino-desacetoxycephalosporanic acid-1β-oxide derivatives wherein the 7β-acylamino substituent suitably is the same as a 6β-acylamino-substituent of penicillins producable by fermentation such as pheny-acetyl and phenoxyacetyl amino, but can also comprise a benzoyl or formyl as substituent $R_3'$. In this process, the deoxygenation process of the invention is used in the last step. The preceding steps leave remainders of various chemicals which generally impeded satisfactory deoxygenation by prior art processes, in that the final yields were not good enough when using normal amounts of the agents involved, while significant improvement of yields, if possible at all, required uneconomical excesses of such agents and often also extended reaction times.

Surprisingly and in contradistinction with prior art processes, the new deoxygenation of the invention generally proved to be applicable without such uneconomic interventions. Even when using silylated intermediates, its accommodation in this multi-step one-pot synthesis fortunately required little or no changes in the relative amounts of chemicals used, in reaction times and in reaction temperatures as compared with application in single step experimentation.

Accordingly, the third object of the invention relates to a process for the synthesis of 7β-acylamino-3-substituted methyl cephalosporanic acid derivatives of the formula

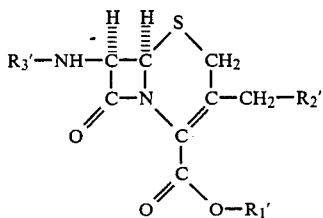

IIa optionally comprising removal of "carbon" ester residues $R_1'$ to give compounds of formula IIa wherein $R_1'$ is hydrogen or a salt forming cation, $R_1'$ is hydrogen or a salt forming cation or a "carbon" ester residue as defined above, $R_2'$ is (lower)alkoxy, (lower)alkylthio, (lower)alkanolyloxy, (lower)alkanoylthio, bromo when $R_1'$ is a "carbon" ester residue, a 1-pyridinium group optionally having substituents attached to the heterocyclic ring, or an optionally substituted heterocyclicthio group as defined above, implicating that silyl groups optionally introduced to protect hydroxy, carboxy and sulfo and/or silyl groups or acyl groups optionally introduced to protect unsaturated heterocyclic secondary amine groups are removed to give the free substituent or salts thereof, and $R_3'$ is formyl or a group as defined above.

According to the third object of the invention, such a multi-step process for the preparation of compounds of formula IIa is characterized in that 75-acylamino-3-methyl-3-cephem-4-carboxylic acid-1β-oxide derivatives of the formula

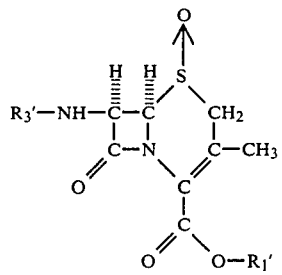

Ib wherein $R_1'$ is hydrogen or a salt forming cation, or a "carbon" ester residue as defined above, and $R_3'$ is formyl or a group as defined above are converted without isolation of intermediates by sequentially the following steps, optionally performed in the same reaction vessel:

(a) a silylation of the carboxy group to introduce a silyl like trimethylsilyl or dimethylsilyl via carboxylate oxygen attached to an additional cephalosporanyl moiety of formula Ib, optionally carried out in situ, when starting with a compound of formula Ib wherein $R_1'$ is not a "carbon" ester group, (b) a light-induced bromination of the 3-methyl group of a compound of formula Ib to give a compound with the 3-bromomethy group using a N-bromo-amide or a N-bromo-imide as brominatin agent, (c) if necessary, as determined principally by the nature of the substituents $R_1'$ and $R_3'$, replacement by hydrogen of bromine atom(s) introduced in step (b) additionally in the methylene group adjacent to the sulfur atom of the dihydrothiazine ring by reaction with a trialkyl or triaryl phosphite, (d) unless it is desired to prepare compounds of formula IIa wherein $R_1'$ is a "carbon" ester residue and $R_2'$ is bromo, an introduction of the substituent $R_2'$ by replacement of the bromine atom introduced in step (b) in the methyl group, and (e) a deoxygenation of the sulfoxy group using phosphorus pentachloride in the presence of in any case an olefinic compound having at least one carbon-carbon double bond with no more than two hydrogen atoms attached thereto which removes chlorine predominantly by way of addition to a carbon-carbon double bond, and optionally in the presence of added or already present catalyst or additive.

If it is desired to operate the process of this third object of the invention without using "carbon" esters for protection of the 4-carboxyl group of the cephalosporin moiety, protection of this group is introduced preferably by silylation to be performed in the first step (a) suitably by an in situ procedure. If the starting material is a salt, e.g. a sodium salt or a triethylamine salt, a monohalosilane like trimethyl chlorosilane or dimethylmethoxy chlorosilane is added to the suspension of the salt in a suitable anhydrous organic solvent. A dihalosilane like dimethyl dichlorosilane can also be used in such a way that the product preponderantly is exclusively a dicephalos-poranyl dimethylsilane.

If the starting material is a cephalosporanic acid-1β-oxide, the silylation can be carried out with the same chlorosilane agents while adding a substantially equivalent amount of a suitable tertiary amine like triethylamine. In view of minimizing remaining amounts of chemicals, particularly with regard to most adequate and fluent operation of step (b), it is however preferred to effect silylation by means of substantially the process described in EPC 0 043 630 which is included by reference herein using as silylation means a balanced amount of a preferably low boiling hexa substituted disilazane of the general formula.

(UVW)Si—NH—Si(UVW)

wherein UVW suitably are lower alkyl and/or lower alkoxy groups like methyl and methoxy while adding a suitable strong silylation catalyst like saccharine.

This silylation catalyst proved to be satisfactorily enough upon incorporation as the first step in the multistep one-pot processes of the present invention on a reduced scale. However with regard to a simple operation of the whole process, a silylation step exactly as indicated in EPC No. 0043630 was found to be not sufficiently reliable and reproducible during application on an industrial scale under the selective and optimized conditions involved. A major problem appeared to be related to the more difficult complete removal and/or incapacitation of the last remnants of ammonia developed during the silylation on a large scale since even very small remaining quantities of not sufficiently incapacitated ammonia appeared to disturb the subsequent bromination step. A relatively minor problem arose occasionally with diligent maintenance of silyl protection throughout the whole process, particularly when performing the bromination step as circumscribed furtheron.

By trial and error, it was surprisingly found possible to circumvent such problems by changing the conditions of the silylation of the starting desacetoxycephalosporanic acid-1β-oxide derivative with a hexasubstituted disilazane in a halogenated hydrocarbon solvent, e.g. dichloromethane so that the silyation mixture contains in addition not only a preferably relatively strong silylation catalyst like saccharine in relative amounts of 0.005 to 5 mol % but also an organic compound in relative amounts of 1 to 50 mol %, which organic compound is prone to silylation by e.g. hexamethyl disilazane under the influence or e.g. saccharine. Preferably, the additional organic compound is introduced in an amount greater than the amount of e.g. saccharine.

The additional organic compound in the first approach has the function of facilitating removal of ammonia in gaseous form, and/or binding the ammonia e.g. by way of forming a sufficiently strong complex or salt, thereby incapacitating the ammonia. In a second approach, it was found to be expedient that the additional compound is also prone to silylation so that it can remove the usually introduced small excess of the hexasubstituted disilazane, but not in such a way that its silylation proceeds at the cost of complete silylation of the desacetoxycephalosporin moiety. The latter means that the silyl derivative of the additional organic compound can act as silylating agent for the desacetoxycephalosporin moiety while it also preferably is more reactive to air-moisture than the silylated desacetoxycephalosporin-1β-oxide derivative, the leakage of which air-moisture is difficult to prevent completely during operations on industrial scale.

Preferred agents in this respect are the usually somewhat acidic compounds belonging to the following classes which essentially constitute relatively weaker silylation catalysts according to the invention of EPC No. 0043630: open imides like 3,3 dimethyl glutarimide or saturated cyclic imides like succinimide, open acyl ureas like 3-benzoyl-1-phenyl-urea or saturated cyclic acyl ureas like hydantoine, and open or saturated cyclic N-sulfonyl carbonamides. These compounds contain an NH radical between two acyl type radicals (carbonyl or sulfonyl). An especially preferred agent in this respect is succinimide.

To indicate what is meant by a relatively strong silylation catalyst, attention is directed to lines 4–19 of page 6 of EPC No. 0043630 containing an enumeration of suitable catalysts, and to lines 20–23 of that page indicating the particularly preferred catalysts. The above indicated compounds in the general sense are relatively weaker silylation catalystsas revealed by the example of EPC No. 0043630, for instance by the tables to the Examples 7 and 85 therein.

It will be appreciated by one skilled in the art that silylation with hexamethyl disilazane using a small to very small relative amount of a relatively strong silylation catalyst like saccharine in combination with, what normally will be the case, a substantially larger amount of e.g. succinimide is not the same as silylation in the presence of saccharine while employing a mixture of e.g. hexamethyl disilazane in equivalent amount and in addition trimethylsilyl succinimide prepared separately, which alternative is possible according to EPC No. 0047560 (Example 1 therein for instance), particularly since the additional use of succinimide does not require the use of larger amounts of hexamethyl disilazane.

It will also be appreciated that an improvement in the silylation conditiohs of the above described nature can be achieved similarly and also practically by introducing a combination of 0.005 to 5 mol % of a suitable strong silylation catalyst like saccharine with a somewhat less than equivalent amount of a hexasubstituted disilazane and a relatively smaller equivalent amount of a silyl derivative of a weaker silylation catalyst as indicated above, e.g. N-trimethylsilyl-succinimide. In other words, when as normally will be the case, the starting desacetoxy-cephalosporin-1β-oxide derivative contains one silylatable group in need of protection, i.e. in general the 4-carboxyl group, there will then be used relative to the amount of cephalosporin about 0.8 to at most 1 equivalent (or about 40 to at most 50 mol %) or the disilazane in combination with 0.01 to about 0.5 equivalent (or usually 1 to about 50 mol %) of e.g. N-trimethylsilyl-succinimide so that an excess of 0.01 to 0.3 silyl group equivalent is employed. This good alternative may seem less economical since it relates to the use of a second silylation agent to be prepare separately, but its advantage may be inter alia that in comparison less of succinimide moiety may be present in the mixture.

It is possible in principle to use cephalosporanic acid 1α-oxides, but the use of the corresponding 1β-oxides usually result in better final yields and the 1β-oxides are also easier to prepare in general.

By large scale fermentation, penicillins can be obtained having as 6β-substituent generally the group,

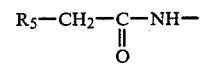

in which $R_5$ can be varied quite substantialy. Such penicillins can be transformed economically and in high yield, via their 1 β-oxides, to the correspondingly substituted 3-methyl-cephalos poranic acids (also named desacetoxycephalosporins) by processes well known in the art. After conversion into their 1β-oxides, such desacetoxycephalosporanic acids are the economically most suited starting materials, particularly when $R_5$ is phenyl or phenoxy. Conceivably, $R_5$ may comprise substituents in need of protection, like in particular hydroxy, which can be silylated easily as well in step (a).

Depending on the nature of $R_5$ and $R_1'$ and the precise conditions of step (b), some material can be lost by a certain degree of concomitant bromination in the methylene group of the substituent $R_5$—$CH_2$, which bromine substituent is at best only partially replaced by hydrogen in step (c). If it is desired to eliminate anyhow this side reaction, another substituent $R_3'$ can be used such as formyl or benzoyl which substituents are not brominated to any hindering extent.

Particularly in view of the circumstance that the process of this third object yet does not comprise a side chain splitting final step, some variation in the solvent used throughout is possible. Generally most suited are halogenated hydrocarbons, preferably low boiling examples such as chloroform, or more suitably 1,2-dichloro-ethane, and most suitably dichloromethane.

The light induced bromination step (b) essentially is the same as the one described in the process of EPC No. 0 034 394 which is included by reference herein. Depending on the scale of the experiment and on constructional angles, the irradiation can be performed for instance in one unit, or in a series of units through which the solution is passed by pumping from a reservoir container which can be cooled to give an almost uniform internal temperature in all irradiation units, from which tiny samples can be taken to verify analytically the progress of the bromination for instance by running a nuclear magnetic resonance spectrum, and which was used conveniently to carry out the preceeding silylation step.

As is described in EPC No. 0 034 394, it is generally efficaceous to introduce before starting the irradiation an additive which destroys or neutralizes small remaining amounts of the silazane employed or of degradation products thereof. Suitably this additive is sulfaminic acid. As indicated in the same patent application, any of the known agents in the art use for thermal, peroxide catalyzed or light induced bromination of reactive carbon-hydrogen bonds can be used such as N-bromo-carbon amides like N-bromo-acetamide and N-bromo-caprolactam or N-brom carbonimides like N-bromo-phthalimide or 1,3-dibromo-hydantoin or N-bromo-sulfonamides and N-bromo-sulfonimides like N-bromosaccharine. Preferably, the brominating agent is N-bromo-suc-cinimide.

Complete or substantially complete bromination of the methyl group attached to 3-ring carbon atom of the dihydrothiazine ring is usually accompanied by some bromination of the methylene group adjacent to sulfur, the extent of which side reaction is influenced by the precise conditions and by the nature of $R_3'$ and $R_1'$. Bromine introduced additionally in this methylene group often has to be replaced by hydrogen to arrive at relatively good final yields and this can be carried out in step (c) with the help of the process described in EPC No. 0 001 149 which is included by reference herein, using in general phosphines like trialkyl and triaryl phosphites. Tributyl phosphite was found to be suitable throughout.

Since esters of 7β-substituted-3-bromomethyl-3-cephem-4-carboxylic acid per se are versatile and valuable tools in the field of cephalosporin chemistry, the present process of the third object of the invention is adaptable to synthesis and isolation of such compounds by directly applying the deoxygenation step (e) after step (c) while omitting the substitution step (d). To some extent, this aspect is compatible with using silyl protection of the carboxy group, but in view of the well-known tendency of 3-bromomethyl-3-cephem-4-carboxylic acids to form fused lactone derivatives by intramolecular cyclization which is difficult to prevent completely, it is preferred to use protection by "carbon" esters. It is somewhat preferred to use in this respect for $R_1'$ t-butyl.

In step d), the bromo atom of the 3-bromomethyl group is replaced by $R_2'$ by procedures generally known per se. To increase when necessary the velocity of the substitution reaction and/or to enhance the solubility of some $R_2'$ containing agents, a minor volume of a substantially anhydrous, highly dipolar aprotic solvent like N,N-dimethylformamide, N-methyl-pyrrolidinone and hexamethyl phosphoric triamide can be introduced since relativel small amounts of such solvents will not seriously impede fast and rewarding performance of the subsequent deoxygenation process of the invention and may even provide for catalysis of the deoxygenation.

In this respect, a presently important collection of final products of formula IIa contain for $R_2'$ an usually unsaturated heterocyclic thio group. Such thiols can be brought to reaction in the presence of a nearly equivalent amount of a suitable tertiary amine like triethyl amine or N,N-dimethyl-aniline or also suitably can be introduced as a corresponding thiolate, e.g. a metal thiolate like the sodium or the potassium thiolate. According to EPC No. 0047560 which is included by reference herein, it is possible and in the context of the process for the preparation of compounds of formula IIa occasionally advantageous indeed to carry out this substitution reaction while using as thiolating agent the corresponding trimethylsilylthio ether. If so desired, the reaction time can be reduced and/or the reaction temperature normally falling in the range between $-10°$ and $+25°$ C., can be lowered by adding to the reaction between the 3-bromomethylcephalosporin intermediate and the trimethylsilylthio ether hexamethylphosphoric triamide in significantly less than equivalent amount-smaking appropriate use of the invention described in EPC No. 0091141 which is included by reference herein.

It will be appreciated that this particular modification involving the use of trimethylsilylthio ethers can be particularly effective if the heterocyclic moiety of the thiol contains a substituent in need of protection occasionally to obtain maximum yields like hydroxy, carboxy and the like, which substituents are then silylated together with the thiol group preferentially using hexamethyl disilazane and catalyst.

In the final step (e) of the new deoxygenation process of the invention using olefinic compounds within a reduced scope, approximately as indicated for application in the process of the second object of the invention, in that in view of adequate accommodation with the preceding steps, it is preferred to use olefinic compounds which take up chlorine fast as well as preponderantly to exclusively by way of addition. Therefore, though at individually appropriately developed conditions, the generally fast reacting terminal olefins with an additional substituent on the inner unsaturated carbon atom can be used, and generally dienes can be employed too. It is preferred to use a monoolefinic compound having a non-terminal carbon-carbon double bond placed in a chain of 4 to 12 carbon atoms optionally substituted at one or at both unsaturated carbon atoms with a methyl or ethyl group or in a carbocyclic ring of 5 to 8 ring atoms optionally substituted at one unsaturated carbon atom with a methyl or ethyl group. For reasons of general efficiency and high conversion and isolation yields, cis-cyclooctene again appeared to be a singularly suitable olefin.

It will be appreciated from the discussion presented before that it is generally preferred to operate the deoxygenation step while deliberately adding a catalyst. Very good catalysts are N,N-dialkylformamides of which it is usually not necessary to use more than 30 mole % with respect to the amount of cephalosporin introduced. It is also possible to provide for deliberate catalysis by adding in similar relative amounts some tertiary amines, particularly a N,N-dialkylarylamine, acknowledging that then a minor part of the chlorine is taken up by substitution of the aromatic nucleus of e.g. N,N-dimethyl-aniline. It is also possible to combine such catalytic additives, e.g. to introduce minor amounts of e.g. N,N-dimethylformamide as well as of N,N-dimethylaniline. It is inferred again, that depending on the precise conditions of one or more of the preceding steps, particularly with respect to the ingredients of steps (a) and (d), deliberate catalysis of step (e) occasionally can be deleted.

It will be appreciated that the deoxygenation process of the present invention is related primarily to the use of an at least equivalent amount of the olefinic compound as chlorine-capturing agent, not taking into account, that in practice it may be quite well possible to develop an equally suitable deoxygenation procedure while deliberately combining a substantially less than equivalent amount of the olefin together with another type of chlorine-capturing agent, for instance an enamine or N,N-dialkyl-aromatic amine or even pyridine, which additional agent consumes chlorine by another type of chemical binding. Such interventions are hereby not considered to constitute a result of independent inventive approach.

As has been indicated in the beginning, it was the primary object of the present invention to develop suitable, versatile and mutually adaptable conditions of various conversions participating in a multi-step synthesis, preferably carried in one and the same reaction vessel, of various 7$\beta$-amino-3-substituted methyl-3-cephem-4-carboxylic acid derivatives starting from certain 7$\beta$-acylamino-3-methyl-3-cephem-4-carboxylic acid-1-oxide derivatives, particularly relating to the more easily attainable 1$\beta$-oxides and in regard to the nature of the 7$\beta$-acylamino substituent to readily available or economically preparable starting materials, which overall synthesis therefore would not involve isolation of any intermediate, and which synthesis in addition would be amenable to lasting protection of e.g. the cephalosporin-4-carboxyl group by preferably silylation suitably applied in situ, whereby a major consideration related to effective and fluent insertion of a sulfoxide deoxygenation step for which a new process had to be developed.

From the rewarding application of the newly found deoxygenation process in the second object of the invention relating to the one-pot preparation of 7$\beta$-amino-3-substituted-3-cephem-4-carboxylic acid derivatives from 7$\beta$-acylamino-3-substituted-3-cephem-4-carboxylic acid-1-oxide derivatives, and in the third object of the invention dealing with the preparation of 7$\beta$-acylamino-3-substituted methyl-3-cephem-4-carboxylic acid derivatives from 7$\beta$-acylamino-3-methyl-3-cephem-4-carboxylic acid-1$\beta$-oxide derivatives, the impression could emerge perhaps, that combination of the results of both preceding objects to give the fourth object of the invention, i.e. overall synthesis of 7$\beta$-amino-3-substituted methyl-3-cephem-4-carboxylic acid derivatives from 7$\beta$-acylamino-3-methyl-3-cephem-4-carboxylic acid-1$\beta$-oxide derivatives carried out without isolation of intermediates would not involve any additional inventive step.

However, it will be appreciated that it could not be predicted witout more that the final side chain splitting step can be carried out without impeding or economically unattractive accommodation of this last step in view of the presence of possibly hindering relatively considerable amounts of a number of chemicals remaining from the first steps of the third object of the invention, e.g. in particular succinimide, trimethylsilyl succinimide, the excess of the phosphite employed in substantial excess, and the basically not well-known by-products originating from the consumed amount of the phosphite in step (c).

Henceforth, the fourth object of the invention relates to a process for the synthesis of 7$\beta$-amino-3-substituted methylcephalosporanic acid derivatives of the formula

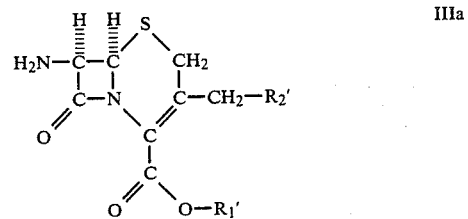

IIIa optionally comprising, isolation of the final products in the form of acid addition salts using a commonly used strong mineral or organic acid, and removal of "carbon" ester residues $R_1'$ to give compounds of formula IIIa wherein $R_1'$ is hydrogen or a salt forming cation wherein, $R_1'$ is hydrogen or a salt forming cation or a "carbon" ester residue as defined above, and $R_2'$ is as defined above.

According to this fourth object of the invention, such a multi-step process for the preparation of compounds of formula IIIa is characterized in that 7$\beta$-acylamino-3-methyl-3-cephem-4-carboxylic acid-1$\beta$-oxide derivatives of formula Ib wherein the substituents $R_1'$ and $R_3'$ are as defined as above with the exception that $R_3'$ does not include formyl are converted without isolation of intermediates by sequentially the following steps optionally performed in the same reaction vessel:

(a) a silylation of the carboxy group optionally carried out in situ when starting with a compound of formula Ib wherein $R_1'$ is hydrogen or a salt forming cation, (b) a light-induced bromination of the methyl group as described and indicated before, (c) if necessary, as circumscribed before, a selective debrominating reaction with the help of an triorganic phosphite, (d) an introduction of $R_2'$ unless while using a "carbon" ester residue $R_1'$, it is chosen to preserve bromine as substituent $R_2'$ in a final product of formula IIIa, (e) a deoxygenation of the sulfoxy group as circumscribed before and, (f) a deacylation reaction splitting the 7β-acylamino substituent by known procedures with the help of phosphorus pentachloride as circumscribed before.

It was found experimentally possible to carry out the entire sequence of steps in one and the same reaction vessel up to the final hydrolysis, which for at least a part can also be performed in the same vessel, whereby, as will be appreciated by persons skilled in the art, in larger scale operations it can be technologically advantageous to use this reaction vessel as the central supply for the light-induced bromination operated in a series of irradiation units by recycling. The final products of formula IIIa are isolated by methods known per se, optionally including hydrolytic or reductive fission of "carbon" ester residue $R_1'$. As with the third object, it is also in the fourth object of the invention preferred to operate with a "carbon" ester in case of preservation of bromine as substituent $R_2'$.

The process description for the steps (a) to (e) is the same as the one given for those steps of the third object of the invention and very similar to or identical also are the preferred ways of operation and the preferences indicated for e.g. solvent, temperature, and chemicals such as the olefinic compounds more suitably applied in the deoxygenation step (e). Since accommodation of the final step (f) surprisingly did not involve specifically adapted measures, this step can be performed as the step (c) of the second object of the invention using methods known in the art.

Preferably starting from 7β-phenylacetamido-(or phenoxyacetamido)-3-methyl-3-cephem-4-carboxylic acid-1β-oxide derivatives, a preferably prepared compound of the formula IIIa is 7β-amino-3-acetoxymethyl-3-cephem-4-carboxylic acid (7-ACA) whereby it is preferred to operate wherein $R_1'$ is t-butyl instead of another "carbon" ester group or a "silyl" group so that the primarily isolated final compound suitably is the t-butyl ester of 7-ACA or a salt thereof containing a strong mineral or organic acid.

Generally, it is preferred to operate the process with "silyl" protection of the cephalosporin carboxyl group by using e.g. the trimethylsilyl group. Preferably using "silyl" protection throughout, while most suitably starting from desacetoxycephalosporin-1-oxides having the 7β-phenylacetamido or the 7β-phenoxyacetamido group, the preferably prepared final compounds of formula IIIa, optionally comprising isolation in the form of a salt, are:

7β-amino-3-(1-methyl-(1H)-tetrazol-5-yl-thiomethyl)-3-cephem-4-carboxylic acid,
7β-amino-3-(1-(2-dimethylamino)ethyl-(1H)-tetrazol-5-yl-thiomethyl)-3-cephem-4-carboxylic acid,
7β-amino-3-(1-sulfomethyl-(1H)-tetrazol-5-yl-thiomethyl)-3-cephem-4-carboxylic acid,
7β-amino-3-(1-carboxymethyl-(1H)tetrazol-5-yl-thiomethyl)-3-cephem-4-carboxylic acid,
7β-amino-3-(1,2,3-(1H)-triazol-5-yl-thiomethyl)-3-cephem-4-carboxylic acid,
7β-amino-3-(5-methyl-1,3,4-thiadiazol-2-yl-thiomethyl)-3-cephem-4-carboxylic acid,
7β-amino-3-(1,3,4-thiadiazol-2-yl-thiomethyl)-3-cephem-4-carboxylic acid,
7β-amino-3-(2,5-dihydro-6-hydroxy-2-methyl-5-oxo-1,2,4-triazin-3-yl-thiomethyl)-3-cephem-4-carboxylic acid.

Again preferably using "silyl" protection during the process, the most preferred final product is 7β-amino-3-(1-methyl)-(1H)-tetrazol-5-yl-thiomethyl)-3-cephem-4-carboxylic acid.

In the following examples there are described several preferred embodiments to illustrate the invention. However, it should be understood that the invention is not intended to be limited to the specific embodiments.

EXAMPLE I

Deoxygenation of 7β-phenylacetamido-3-methyl-3-cephem-4-carboxylic acid 1β-oxide employing cycloheptene To a suspension of 3.48 g (purity 96% by weight: 9.59 mmol) of 7β-phenylacetamido-3-methyl-3-cephem-4-carboxylic acid 1β-oxide in 40 ml of dichloromethane, which was kept under nitrogen, 2.3 ml (18.09 mmol) of trimethyl chlorosilane and 2.3 ml (17.75 mmol) of N,N-dimethylaniline were added with stirring at 0° C. The temperature was raised to about 20° C., followed by stirring during 30 minutes. The mixture was cooled to −60° C., followed by sequential introduction of 1.3 ml (11 mmol) of cycloheptene and 2.4 g (11.5 mmoles) of phosphorus pentachloride, whereupon the mixture was stirred additionally during 15 minutes at −45° C. Stirring was continued during cautious addition of 10 ml of water and subsequently during 15 minutes at −10° C. Addition of 30 ml of toluene and stirring for 3 hours at −5° C. afforded a precipitate, which was collected by filtration, followed by washings with toluene and water, and by drying in vacuo to constant weight. Isolated weight 2.92 g of 7β-phenylacetamido-3-methyl-3-cephem-4-carboxylic acid. The identity of the isolated product was checked by TLC and PMR. A purity of 97% by weight resulted from HPLC assay, corresponding to isolation of 8.52 mmoles.

While accounting for the purity of the starting material the yield is 88.9%. According to HPLC assay the combined filtrates still contained an amount of desired product equivalent to 7.1%. The total conversion yield therefore was 96%.

PMR (pyridin-d₅, δ-values in ppm, 60 Mc, TMS): 2.12 (s, 3H); 3.01, 3.32, 3.41 and 3.72 (AB-q, J=18 Hz, 2H); 3.83 (s, 2H); 5.18 (d, J=4.5 Hz, 1H); 6.19 (dd, J=4.5 Hz, J=8 Hz, 1H); 7.13 to 7.58 (m, 5H); 10.06 (d, J=8 Hz, about 1H); 10.16 (s, about 1H).

IR (KBr-disc, values in cm⁻¹): 3270, 3060, 1760, 1700, 1665, 1626 and 1545.

EXAMPLE II

Deoxygenations of 7β-phenylacetamido-3-methyl-3-cephem-4carboxylic acid 1β-oxide employing cis-cyclooctene (a) The first experiment was an exact replica of the experiment described in Example I but for one alteration: the 11 mmol of cycloheptene were replaced by 10 mmol (1.3 ml) of cis-cyclooctene. The isolated weight was 2.98 g, amounting to an isolation yield of 89.7% in view of a purity of 96% by weight as determined by HPLC assay. According to HPLC assay the combined filtrates still contained an amount of desired product equivalent to 9.4%. While accounting for the purity of the starting material (96% by weight) the overall conversion yield therefore was 99.1%.

(b) The experiment was repeated in exactly the same way. The isolation yield was 3.02 g. Direct isolation amounted to a yield of 92.4%, taking into account its purity (HPLC assay: 97.5%) and the purity of the starting material (96%).

(c) The experiment was repeated on a double scale (6.96 g of the sulphoxide) employing otherwise identical conditions. The direct isolation yield was 5.91 g, or 91.2% while accounting for its purity (97.5% according to HPLC assay) and for the purity of the starting material. The mother liquor contained a further 3.0% of desired product. The total conversion yield therefore was 94.2%.

(d) Experiment (c) was repeated on the same scale employing the same conditions but for one alteration. Instead of 40 ml of toluene, now 40 ml of n-hexane were added followed by 3 hours stirring at 0° C. The precipitate was collected by filtration, washed with n-hexane and water, and dried in vacuo. The isolated weight was 6.42 g. In view of a purity of 97.5% by weight according to HPLC assay, the direct isolation yield was 97.1%.

EXAMPLE III

Deoxygenation of 7β-phenylacetamido-3-acetoxymethyl-3-cephem-4-carboxylic acid 1β-oxide employing cis-cyclooctene This experiment was performed on approximately the same scale was in Example I, while using the same operational method described therein. Used were: 4.06 g (8.59 mmoles in view of a purity of 86% according to HPLC assay) of the starting sulphoxide, 2.4 ml (18.9 mmol) of trimethyl chlorosilane, 2.4 ml (18.5 mmol) of N,N-dimethylaniline, 40 ml of dichloromethane, 1.3 ml (10 mmol) of cis-cyclooctene, 2.4 g (11.5 mmol) of phosphorus pentachloride, 10 ml of water and 30 ml of toluene. Isolated weight of substantially dry product was 3.48 g. The purity of 90.5% by weight as determined by HPLC assay indicated the presence of 8.07 mmol of 7β-phenylacetamido-3-methyl-3-cephem-4-carboxylic acid in the isolated product. The actual isolation yield therefore is 94%. It was established by means of HPLC assay, that the combined filtrates still contained 3.9% of the desired compound. The overall conversion yield therefore was 97.9%. The product was identified by TLC, PMR and IR.

PMR (DMSO-$d_6$, δ-values in ppm, 60 Mc, TMS): 2.04 (s, 3H); about 3.6 (4H); 4.59, 4.80, 4.95 and 5.16 (AB-q, J=13 Hz, 2H); 5.08 (d, J=4,5 Hz, 1H); 5.69 (dd, J=4.5 Hz, J=8 Hz, 1H); 7.27 (s, 5H); 9.04 (d, J=8 Hz, about 1H).

IR (KBr-disc, values in cm$^{-1}$): 3265, 3050, 1785, 1752, 1740, 1715, 1662, 1230.

EXAMPLE IV

Deoxygenation of 7β-phenylacetamido-3-(5-methyl-1,3,4-thiadiazol-2-yl)thiomethyl-3-cephem-4-carboxylic acid 1β-oxide employing cis-cyclooctene According to HPLC assay the starting material has a purity of 85% by weight. To a suspension of 8.00 g (therefore 14.21 mmol) of the sulphoxide in 80 ml of dichloromethane, which was kept under nitrogen, 4.6 ml (36.2 mmol) of trimethyl chlorosilane and 4.5 ml (35.5 mmol) of N,N-dimethyl-aniline were added with stirring at 0° C. The temperature was raised to 20° C., followed by stirring during 30 minutes. The mixture was cooled to −66° C., followed by sequential introduction of 2.6 ml (20 mmol) of cis-cyclooctene and 3.9 g (18.7 mmol) of phosphorus pentachloride, whereupon the mixture was stirred additionally during 10 minutes at −45° C. After addition of 5 ml of N,N-dimethyl-formamide, 20 ml of water were added cautiously while stirring continuously. In the mean time the cooling bath was removed, and the layers were separated after the mixture had attained −5° C. While adjusting the pH to 7 by addition of dilute ammonia, the organic phase was extracted a few times with a total volume of 60 ml of water. The organic phase was discarded, whereupon the combined water-layers were diluted with 50 ml of cold methanol. While maintaining pH 2 by controlled addition of 4N hydrochloric acid, the solution prepared was given gradually and slowly to a stirred mixture of 20 ml of water and 20 ml of methanol. After standing for a while at 0° C., the precipitated product was collected by filtration, followed by washing with cold water and drying to constant weight in vacuo. Isolated were 7β-phenylacetamido-3-(5-methyl-1,3,4-thiadiazol-2-yl)thiomethyl-3-cephem-4-carboxylic acid in crude form. According to HPLC assay the purity of the isolated product was 87.5% by weight. The yield therefore was 12.48 mmol or 89%. The mother liquor contained another 2% of desired product. The total conversion yield therefore was 91%.

PMR ($d_6$-DMSO, δ-values in ppm, 60 Mc, TMS): 2.67 (s, 3H); 3.52 (s, 2H); 3.35, 3.65, 3.68 and 3.98 (AB-q, J=18 Hz, 2H); 4.10, 4.30, 4.43 and 4.63 (AB-q, J=12.5 Hz, 2H); 5.06 (d, J=8.5 Hz, 1H); 5.70 (dd, J=4.5 Hz, J=8.5 Hz, 1H); 7.28 (5H); 9.14 (d, J=8.5 Hz, about 1H).

IR (KBr-disc, values in cm$^{-1}$): 3280, 3035, 1777, 1720, 1661, 1535, 1500 and 1458.

EXAMPLE V

Deoxygenation of 7β-phenylacetamido-3-(1-methyl-1H-tetrazol-5-yl)thiomethyl-3-cephem-4 carboxylic acid 1β-oxide employing cis-cyclooctene (a) The starting material was converted in exactly the same way as described in example IV. Employed were 5.24 g of crude starting material, according to HPLC assay containing 9.99 mmol (the sample had a purity of 88.2% by weight), 2 ml (15.7 mmol) of trimethyl chlorosilane, 2 ml (15.4 mmol) of N,N-dimethylaniline and 40 ml of dichloromethane, the resulting mixture was cooled to −60° C., followed by sequential introduction of 1.4 ml (10.8 mmol) of cis-cyclooctene and 2.4 g (11.5 mmol) of phosphorus pentachloride, and stirring during 15 minutes at −50° C. 10 ml of water were added cautiously. After introduction of 2 ml of N,N-dimethylformamide the mixture was stirred for 15 minutes at −10° C. 30 ml of toluene were added, followed by 3 hours stirring at −5° C. The precipitate formed was filtered off, washed with cold water and toluene, and thereafter dried in vacuo. The product weighed 4.76 g. According to HPLC assay 85% of the product was 7β-phenylacetamido-3-(1-methyl-1H-tetrazol-5-yl)thiomethyl-3-cephem-4-carboxylic-acid, corresponding with a yield of 90.8%. The mother liquor according to HPLC assay contained another 6.3% of the desired compound. The total conversion yield therefore was 97.1%.

PMR (mixture of CDCl$_3$ and $d_6$-DMSO, δ-values in ppm, 300 Mc, TMS): 3.56, 3.60, 3.62 and 3.66 (AB-q, J=14 Hz, 2H); 3.67 (s, 2H); 3.94 (s, 3H); 4.28, 4.32, 4.34 and 4.38 (AB-q, J=13.5 Hz, 2H); 4.96 (d, J=5 Hz, 1H); 5.74 (dd, J=5 Hz, J=8.5 Hz, 1H); 7.21-7.34 (m, 5H); 8.27 (d, J=8.5 Hz, about 1H).

IR (KBr-disc, values in cm$^{-1}$) 3260, 1780, 1725, 1657, 1619, 1535, 1492, 1155, 1085.

(b) For comparison of the process of the present invention with a method known in the art, the example described hereinabove was repeated while replacing ciscyclooctene for N,N-dimethylaniline (10.8 mmol). HPLC assay of a sample was taken directly after 15 minutes additional stirring indicated that the desired compound was formed with 86.6% conversion yield. In the isolation procedure the 3 hours stirring at −5° C. did not afford a crystalline precipitate. Addition of 10 ml of water and 10 ml of dichloromethane resulted in an oily precipitate. The supernatant layer was decanted and the residual oil triturated with 15 ml of dichloromethane to give a solid. While stirring 10 ml of toluene were added at 0° C. Filtration, washing with 1:1 dichloromethane - toluene and drying in vacuo gave 4.92 g of the desired compound with a purity of only 66.5% by weight. The isolation yield therefore was 73.4%. The mother liquor still contained about 13% of good product. A yield of conversion of about 86.5% was thereby confirmed.

EXAMPLE VI

Deoxygenation of t-butyl-7β-phenylacetamido-3-methyl-3-cephem-4-carboxylate 1β-oxide employing cis-cyclooctene At −20° C. 1.3 ml (10 mmol) of cis-cyclooctene and 2.4 g (11.5 mmol) of phosphorus pentachloride were given to a stirred solution of 4.08 g of t-butyl 7β-phenylacetamido-3-methyl-3-cephem-4-carboxylate 1β-oxide (9.08 mmol in view of 90% purity according to HPLC assay) in 80 ml of dichloromethane. The temperature was lowered to −40° C., followed by 15 minutes stirring. 10 ml of water were added with care, whereupon stirring was continued during 15 minutes at 0° C. The layers were separated, the organic layer was subjected to washings with water, drying on anhydrous magnesium sulphate, filtration and concentration in vacuo to a volume of about 25 ml. Gradual addition of light petroleum resulted in a precipitate. The solid was collected by filtration, washed with light petroleum, and dried in vacuo. 4.1 g of t-butyl 7β-phenylacetamido-3-methyl-3-cephem-4-carboxylate were obtained, corresponding with a yield of 93% in view of according to HPLC assay 80.5% purity.

PMR (CDCl$_3$, δ-values in ppm, 60 Mc, TMS): 1.50 (s, 9H); 2.06 (s, 3H); 2.93, 3.23, 3.36, 3.66 (AB-q, J=18.5 Hz, 2H); 3.61 (s, 2H); 4.90 (d, J=4.5 Hz, 1H);5.75 (dd, J=4.5 Hz and J=9 Hz, 1H); 6.85 (d, J=9 Hz, about 1H); 7.31 (s, 5H).

IR (KBr-disc, values in cm$^{-1}$): 3260, 1780, 1725, 1657, 1619, 1535, 1492, 1155 and 1085.

EXAMPLE VII

Deoxygenation of 7β-phenylacetamido-3-methyl-3-cephem-4-carboxylic acid 1α-oxide employing cis-cyclooctene The procedure used was exactly the same as described under example I. Employed were 0.245 g (maximally 0.70 mmol) of the 1α-oxide of phenylacetamido-desacetoxycephalosporin of unknown quality, 0.14 ml (1.10 mmol) of trimethyl chlorosilane, 0.14 ml (1.10 mmol) of N,N-dimethylaniline, 2.8 ml of dichloromethane, 0.103 ml of (0.79 mmol) of cis-cyclooctene, 0.175 g (0.84 mmol) of phosphorus pentachloride and in the isolation procedure 1.4 ml of toluene. The reaction conditions during the reduction sequence were as usual 15 minutes at −45° C. 0.1579 g of the desired phenylacetamido disacetoxycephalosporin were isolated in solid form. This corresponds with a direct yield of 57% in view of about 84.0% purity as determined by HPLC assay. The mother liquor contained about 15% of the same compound as determined by HPLC assay. The minimal overall conversion yield therefore is about 72%.

EXAMPLE VIII

Variation of olefinic compound employed in the deoxygenation of 7β-phenylacetamido-3-methyl-3-cephem-4-carboxylic acid 1β-oxide via its trimethylsilylester A number of olefinic compounds comprised by the invention were subjected to the same standard procedure. The results of these experiments are collected in Table I, which also refers to an experiment (the last entry) wherein no secondary agent for the capture of chlorine was used, and to two experiments wherein secondary agents known in the prior art, i.e. 1-morpholin-4-yl-cyclohexene and N,N-dimethyl aniline, were employed.

The procedure followed is the one described in example I. The amounts and volumes used were as follows:
6.96 (effectively 19.38 mmol) of 7β-phenylacetamido-3-methyl-3-cephem-4-carboxylic acid 1β-oxide of according to HPLC assay 97% purity,
80 ml of dichloromethane,
4.6 ml (36.2 mmol) of trimethyl chlorosilane,
4.6 ml (35.5 mmol) of N,N-dimethyl aniline,
22 mmol of the olefinic compound or of a prior art agent,
4.8 g (23 mmol) of phosphorus pentachloride.
During after-treatment of the reaction mixture 20 ml water and 40 ml of toluene were added.

Unless stated otherwise all deoxygenations involved 15 minutes reaction at −45° C. By means of HPLC assay all yield percentages were corrected for the actual content of 7β-phenylacetamido-3-methyl-3-cephem-4-carboxylic acid.

TABLE I

Deoxygenation of 7β-phenylacetamido-3-methyl-3-carboxylic acid 1β-oxide via its trimethylsilylester by phosphorus pentachloride in dichloromethane in the presence of an olefinic compound (15 min., −45° C.).

| Exp. | olefinic compound | yield in g | purity (%) | isolation yield (%) | mother liq. (%) | total conv. (%) |
|---|---|---|---|---|---|---|
| 1. | 1-hexene | 4.00 | 96.5 | 60.0 | 3.0 | 63.0 |
| 2. | trans-2-hexene | 5.71 | 98.5 | 87.3 | 2.9 | 90.2 |
| 3. | commercial 2-hexene (a) | 5.63 | 96.5 | 84.3 | 3.8 | 88.1 |
| 4. | 1-octene | 3.89 | 89.5 | 52.7 | 9.4 | 62.1 |
| 5. | trans 2-octene | 5.79 | 99.0 | 89.0 | 2.5 | 91.5 |
| 6. | 2-methyl-1-pentene | 5.44 | 95.5 | 80.7 | 7.0 | 87.7 |

TABLE I-continued

Deoxygenation of 7β-phenylacetamido-3-methyl-3-cephem-4-carboxylic acid 1β-oxide via its trimethylsilyester by phosphorus pentachloride in dichloromethane in the presence of an olefinic compound (15 min., −45° C.).

| Exp. | olefinic compound | yield in g | purity (%) | isolation yield (%) | mother liq. (%) | total conv. (%) |
|---|---|---|---|---|---|---|
| 7. | 2,3-dimethyl-2-butene | 5.88 | 97.5 | 88.9 | 4.2 | 93.1 |
| 8. | cyclopentene | 5.84 | 97.0 | 87.8 | 3.1 | 90.9 |
| 9. | cyclohexene | 4.94 | 94.5 | 72.5 | 5.0 | 77.5 |
| 10. | 1-methyl-cyclohexene | 5.50 | 98.5 | 84.1 | 1.6 | 85.6 |
| 11. | 1-methyl-cyclooctene | 6.11 | 92.5 | 87.7 | 8.5 | 96.2 |
| 12. | cyclododecene | 4.84 | 97.8 | 73.5 | 16.0 | 89.5 |
| 13. | 2-cyano-but-2-ene | 3.40 | 93.5 | 49.3 | 9.2 | 58.5 |
| 14. | 1-morpholin-4-yl-cyclohexene (b) | 5.19 | 85.5 | 68.9 | 10.4 | 79.3 |
| 15. | N,N—dimethyl aniline | 5.59 | 99.0 | 85.8 | 7.0 | 92.8 |
| 16. | none | 4.42 | 80.0 | 54.8 | 3.2 | 58.0 |

(a) Commercial 2-hexene contained besides trans-2-hexene a considerable amount of cis-2-hexene
(b) After 75 min. at −45° C. the results were sequentially as follows: 5.74 g, 99.5%, 88.7%, 3.2% and 91.9%.

EXAMPLE IX

Deoxygenation of t-butyl 7β-phenylacetamido-3-bromomethyl-3-cephem-4-carboxylate 1β-oxide employing cis-cyclooctene At −20° C. 0.325 ml (2.5 mmol) of cis-cyclooctene and 0.6 g (2.9 mmol) of phosphorus pentachloride were given sequentially to a stirred solution of 1.21 g of t-butyl 7β-phenylacetamido-3-bromomethyl-3-cephem-4-carboxylate 1β-oxide (2.33 mmol in view of 93% purity according to HPLC assay) in 25 ml of dichloromethane. After cooling to −40° C. and stirring additionally during 15 minutes, 3 ml of water were added with care, followed by 15 minutes stirring at 0° C. The layers were separated, the organic layer twice washed with 3 ml volumes of iced water, dried on anhydrous magnesium sulphate, filtered and concentrated in vacuo to a volume of about 5 l. Addition of light petroleum (40–60) resulted in a precipitate. The solid was collected by filtration, washed with n-hexane, and dried in vacuo.

1.0 g of t-butyl 7β-phenylacetamido-3-bromomethyl-3-cephem-4-carboxylate were obtained, corresponding with a yield of 85% in view of 92.5% purity according to HPLC assay.S PMR (CDCl$_3$, δ-values in ppm, 60 Mc, TMS): 1.52 (s, 9H); 3.15, 3.45, 3.53 and 3.83 (AB-q, 2H, J=18 Hz, 2H); 3.60 (s, 2H); 4.33 (s, 2H); 4.89 (d, J=4.5 Hz, 1H); 5.76 (dd, J=4.5 Hz and J=9 Hz); 6.46 (d, J=9 Hz, about 1H); 7.27 (s, 5H).

IR (KBr-disc, values in cm$^{-1}$): 3345, 1765, 1705, 655, 1610, 1500, 1360, 1300, 1260, 1200, 1140, 1080, 1000, 35, 710, 690 and 600.

EXAMPLE X

Deoxygenation of 7β-phenoxyacetamido-3-methyl-3-cephem-4-carboxylic acid 1β-oxide employing cis-cyclooctene To a suspension of 7.29 g 7β-phenoxyacetamido-3-methyl-3-cephem-4-carboxylate 1β-oxide (19.7 mmol in view of 98.6% purity according to HPLC assay) in 80 ml of dichloromethane, which was kept unde nitrogen, 4.6 ml (36 mmol) of trimethyl chlorosilane and 4.6 ml (35.5 mmol) of N,N-dimethylaniline were added with stirring at 0° C. After stirring additionally for 30 minutes at room temperature, the reaction mixture was cooled down to −50° C., followed by introduction of sequentially 2.86 ml (22 mmol) of ciscyclooctene and 4.8 g (23 mmol) of phosphorus pentachloride. 15 minutes stirring at −45° C. were followed by careful addition of 20 ml of water and 15 minutes stirring at about −15° C 80 ml of toluene were added and stirring was continued during 3.5 hours at 0° C. The precipitate formed was collected by filtration, washed with water and toluene, and dried in vacuo. Isolated weight 6.37 g of 7β-phenoxyacetamido-3-methyl-3-cephem-4-carboxylic acid (yield 91.7% in view of 98.8% purity according to HPLC assay).

PMR (pyridine-d$_5$, δ-values in ppm, 60 Mc, TMS): 2.14 (s, 3H); 3.02, 3.32, 3.39, 3.69 (AB-q, J=18 Hz, 2H); 5.23 (d, J=4.5 Hz, 1H), 6.19 (dd, J=4.5 Hz, J=8.5 Hz, 1H); 4.81 (s, 2H); 6.78–7.50 (m, 5H); about 9.1 (broad, about 1H); 9.82 (d, J=8.5 Hz, about 1H).

IR (KBr-disc, -values in cm$^{-1}$): 3400, 1755, 1730, 1670, 1592, 1585, 1520, 1492, 1225, 754 and 683.

EXAMPLE XI

Deoxygenation of 7β-phenylacetamido-3-methyl-3-cephem-4-carboxylic acid '-oxide employing dienes The following experiments were performed exactly at the conditions described in Example I. In all experiments were used:
6.93 g of the title compound (19.40 mmol in view of 97.5% purity according to HPLC analysis),
80 ml of dichloromethane,
4.6 ml (36.2 mmol) of trimethyl chlorosilane,
4.6 ml (35.5 mmol) of N,N-dimethylaniline,
4.8 g (23 mmol) of phosphorus pentachloride,
20 ml of water and
40 ml of toluene.

Only the identity and the amount of the diene were varied. All yields were calculated on the basis of the content of the desired product determined by HPLC assay.

(a) The reaction with phosphorus pentachloride was performed in the presence of 1.36 ml (11 mmol) of 1,3-cyclooctadiene. Isolated weight 4.27 g of 7β-phenylacetamido-3-methyl-3-cephem-4-carboxylic acid. Isolation yield 61.9% in view of 93.5% purity by weight according to HPLC assay. The mother liquor contained 8.6% of this compound. The total conversion yield therefore was 70.5%.

(b) The deoxygenation was performed in the presence of 2.72 ml (22 mmol) of 1,3-cyclooctadiene. Isolated weight 4.80 g. Isolation yield 71.5% in view of 96% purity by weight. The mother liquor still contained 5.6% of desired product. Total conversion yield 77.1%.

(c) The reaction with phosphorus pentachloride was carried out in the presence of 1.26 ml (11 mmol) of trans-2-trans-4-hexadiene. Isolated weight 5.86 g. Isolation yield 86.8% in view of 95.5% purity by weight. The mother liquor still contained 6.7% of desired product. The total conversion yield therefore was 93.5%.

(d) The deoxygenation was perfomed in the presence of 2.51 ml (22 mmol) of trans-2-trans-4-hexadiene. Isolated weight 5.75 g. Isolation yield 87.4% in view of 98% purity by weight according to HPLC assay. The mother liquor still contained 4.1% of desired product. The total conversion yield therefore was 91.5%.

(e) The deoxygenation was performed in the presence of 1.24 ml (10 mmol) of 1,5-cyclooctadiene. Isolated weight 4.92 g. Isolation yield 74% in view of 95.5% purity by weight according to HPLC assay. The mother liquor still contained 4.7% of desired product. The total conversion yield therefore was 78.7%.

EXAMPLE XII

Deoxygenation of 7β-phenylacetamido-3-methyl-3-cephem-4-carboxylic acid 1β-oxide in acetonitrile employing ciscyclooctene To a suspension of 6.93 g (19.4 mmol) of the 97.5% pure 1β-oxide in 160 ml of acetonitrile, which was kept under nitrogen, 4.6 ml (36.2 mmol) of trimethylchlorosilane and 2.3 ml (35.5 mmol) of N,N-dimethylaniline were added with stirring at about 0° C. The temperature was raised to about 20° C., followed by 30 minutes stirring. The mixture was cooled down to below −40° C., followed by sequential introduction of 2.86 ml (22 mmol) of cis-cyclooctene and 4.8 g (23 mmol) of phosphorus pentachloride, whereupon the mixture was stirred additionally for 15 minutes at −45° C. Stirring was continued during cautious addition of 20 ml of cold water and subsequently for 15 minutes at −10° C. Acetonitrile was removed azeotropically by concentration in vacuo at about 0° C. Addition of 40 ml of toluene and of 10 ml of cold water resulted in a crystalline precipitate. After 1 hour stirring at 0° C. the product was collected by filtration, washed with cold water and toluene, and dried in vacuo to constant weight. Isolated weight 5.45 g of 7β-phenylacetamido-3-methyl-3-cephem-4-carboxylic acid. Since according to HPLC assay the isolated product had a purity of 97% by weight, the isolation yield was 82%. In view of the presence of another 2.7% of desired product in the mother liquor, the total conversion yield was 84.7%.

EXAMPLE XIII

Preparation of 7β-amino-3-(5-methyl-1,3,4-thiadiazol-2-yl-thiomethyl)-3-cephem-4-carboxylic acid from 7β-phenylacetamido-3-(5-methyl-1,3,4-thiadiazol-2-yl-thiomethyl)-3-cephem4-carboxylic acid 1β-oxide (a) In nitrogen atmosphere 3.6 ml (28.3 mmol) of trimethyl chlorosilane and 3.55 ml (28.0 mmol) of N,N-dimethylaniline were added at 0°–5° C. with stirring to a suspension of 8.0 g (purity 84% by weight, 14.04 mmol) of 7β-phenylacetamido-3-(5-methyl-1,3,4-thiadiazol-2-yl-thiomethyl)-3-cephem-4-carboxylic acid 1β-oxide in 60 ml of dichloromethane. The mixture was stirred at about 20° C. during 30 minutes, whereupon the temperature was lowered to −60° C., followed by sequential introduction of 2.25 ml (17.3 mmol) of cis-cyclooctene and 3.9 g (18.7 mmol) of phosphorus pentachloride. The resulting reaction mixture was stirred for 10 minutes at −45° C., whereupon the temperature was lowered to −55° C., followed by sequential introduction of 5.5 g (26.4 mmol) of phosphorus pentachloride and 3.7 ml (29.2 mmol) of N,N-dimethylaniline. The mixture was stirred for 3 hours at −45° C. The temperature was brought to −60° C., 25 ml of cold isobutanol were added, and stirring was continued during 1 hour at −45° C. After addition of 25 ml of 4N sulphuric acid and stirring for 10 minutes at −10° C. the resulting two-layer system was separated and the organic layer extracted with 20 ml of 2N sulphuric acid. The organic layer was discarded and the combined aqueous layers treated with 2 g of activated carbon. After removal of activated carbon by filtration, the pH was raised to 1.0 by addition of 25% ammonia in water. After 1 hour cooling in ice the precipitate formed was collected by filtration, washed with water and acetone, and dried to constant weight.

Isolated were 4.47 g 7β-amino-3-(5-methyl-1,3,4-thiadiazol-2-yl-thiomethyl)-3-cephem-4-carboxylic acid of according to HPLC assay 92.5% purity by weight. The overall yield therefore was 86%.

(b) Very considerable efforts were undertaken concomitantly in order to arrive at the relatively most suitable accomodation of the known phosphorus trichloride/N,N-dimethyl formamide deoxygenation method in the two-step synthesis of the same final product starting however from a considerably more pure batch of 7β-phenylacetamido-3-(5-methyl-1,3,4-thiadiazol-2-yl-thiomethyl)-3-cephem-4-carboxylic acid 1β-oxide.

By exactly the same procedure described above 19.8 mmol of starting material (present in 10.0 g of according to HPLC-assay 95% purity by weight) were silylated in 70 ml of dichloromethane, using 39.9 mmol of trimethyl chlorosilane and 39.5 mmol of N,N-dimethyl aniline. By necessity employing continuous heavy cooling at −75° to −70° C., the deoxygenation was carried out with 13 mmol of N,N-dimethyl formamide and 31.4 mmol of phosphorus trichloride (added dropwise in 5 minutes) in 20 minutes. While using 55.1 mmol of N,N-dimethyl aniline and 48 mmol of phosphorus pentachloride, the subsequent imidchloride formation was performed in 2.5 hours, starting at −70° C. and finishing at −45° C. The following treatment with isobutanol and water in the usual manner finally yielded 5.82 g of isolated product, having a purity of 94.0% by weight according to HPLC-assay. The overall yield was 80.3%.

For a comparison the most important details of both preparations are collected in Table II appended to example XIV, whereby the amounts of the various agents employed in example (a) are proportionally raised to the level of using 19.8 mmol of starting material instead.

(c) The experiment described under (a) was repeated in exactly the same way but for one alteration: ciscyclooctene was omitted so that the deoxygenation step did not comprise the use of a secondary reduction agent. The hydrolysed reaction mixture contained according to HPLC-assay an amount of the 7β-amino derivative equivalent to a conversion yield of 32%. Finally isolated were 1.0 g of low quality.

(d) The experiment under (a) was repeated in exactly the same way but for one alteration: the 17.3 mmol of ciscyclooctene were replaced by 17.3 mmol of N,N-dimethyl aniline. Isolated were 4.05 g of final product, having a purity of 89.0% by weight according to HPLC assay. The overall yield therefore was 75%.

The with respect to experiment (a) 11% lower yield of isolation is not caused by a relatively less efficient isolation, since the combined mother liquors contained a normal amount of residual product, namely 2.5%.

EXAMPLE XIV

Preparation of
7β-amino-3-(1-methyl-(1H)tetrazol-5-yl-thiomethyl)-3-cephem-4-carboxylic acid from
7β-phenylacetamido-3-(1-methyl-(1H)tetrazol-5-yl-thiomethyl)-3-cephem-4-carboxylic acid 1β-oxide (a) In nitrogen atmosphere 3 ml (23.5 mmol) of trimethyl chlorosilane and 2.95 ml (23.1 mmol) of N,N-dimethylaniline were added at 0° C. with stirring to a stirred suspension of 7.8 g (purity 83% by weight, 14.0 mmol)of 7β-phenylacetamido--3-(1-methyl-(1H)tetrazol-5-yl-thiomethyl)-3-cephem-4-carboxylic acid 1β-oxide in 60 ml of dichloromethane. Subsequently the mixture was stirred at about 20° C. during 30 minutes, and thereafter cooled to −60° C. Sequential addition of 2.05 ml (15.7 mmol) of cis-cyclooctene and 3.6 g (17.3 mmol) of phosphorus pentachloride was followed by 10 minutes stirring at −45° C., and cooling to −60° C. Addition of 4.0 g (19.2 mmol) of phosphorus pentachloride and 3.45 ml (27.2 mmol) of N,N-dimethylaniline was followed by 3 hours stirring at −45° C. The temperature was lowered to −60° C., 25 ml of precooled isobutanol were introduced, and stirring was continued during 1 hour at −45° C. After addition of 25 ml of 4N sulphuric acid and stirring for 10 minutes at −15° C. the resulting two-layer system was separated and the organic layer extracted with 30 ml of 6N sulphuric acid. During extraction a total volume of 70 ml of water was added to dissolve precipitating product. The organic phase was discarded thereafter. After stirring with 2 g of activated carbon and filtration, the clear combined acidic aqueous solution was treated with 25% ammonia in water to give pH 1.5 at about 0° C. Shortly thereafter the precipitated product was collected by filtration, washed with cold water and acetone, and dried to constant weight. Isolated were 4.46 g of 7β-amino-3-(1 methyl(1H)tetrazol-5-yl-thiomethyl)-3-cephem-4-carboxylic acid of 93.0% purity by weight according to HPLC-assay. The overall yield therefore was 90.2%.

(b) In the same way as described in example XIII (b), the phosphorus trichloride/N,N-dimethyl formamide deoxygenation method was optimized to give the relatively most suitable procedure for the synthesis of title compound, while starting from appreciably more pure 7β-phenylacetamido-3-(1-methyl-(1H)tetrazol-5-yl-thiomethyl)-3-cephem-4-carboxylic acid 1β-oxide.

The experiment was performed on a scale of 7.33 mmol of starting compound as present in 3.83 g of 88.5% purity by weight. Used were 25 ml of dichloromethane, 12.3 mmol of trimethyl chlorosilane, 14.6 mmol of N,N-dimethyl aniline, 5.8 mmol of N,N-dimethyl formamide, 12.6 mmol of phosphorus trichloride, 19.2 mmol of phosphorus pentachloride and 25.8 mmol of N,N-dimethyl aniline to give the imidechloride, the solution of which was treated with isobutanol as described under (a). The deoxygenation step had to be performed at −75° to −70° C. (in total 20 minutes) employing heavy cooling. Isolated were 2.15 g of final product of 86.0% purity by weight. The overall yield therefore was 76.4%.

For comparison the most important details of both preparations are collected in Table II together with those of example III, whereby the amounts of the various agents employed in experiments XIV (a) and (b) are raised proportionally to the level of using 19.8 mmol of starting material.

TABLE II

Details of two-step one-pot preparations of the 7β-amino-3-substituted methyl-3-cephem-4-carboxylic acids of Examples XIII and XIV, involving as deoxygenation methods the new PCl5/olefine method (a) or the known PCl3DMF method (b), while starting from 19.8 mmol of the corresponding 7β-phenylacetamido 1β-oxide derivatives (all amounts in mmol).

| Exp. | purity Starting material | silylation TMCS | silylation DMA | 1. deoxygenation temp. °C. (A) | 1. deoxygenation cyclo-octene | 1. deoxygenation PCl5 | 1. deoxygenation DMF | 1. deoxygenation PCl3 | 2. imide-chloride formation PCl5 | 2. imide-chloride formation DMA | total amount of agents in steps 1 + 2 | purity prod. | total yield |
|---|---|---|---|---|---|---|---|---|---|---|---|---|---|
| XIII(a) | 84% | 39.9 | 39.5 | −45 (−60) | 24.4 | 26.4 | — | — | 37.2 | 41.2 | 129.2 | 92.5% | 86.0% |
| XIII(b) | 95% | 39.9 | 39.5 | −70 (−75) | — | — | 13.0 | 31.4 | 48.0 | 55.1 | 147.5 | 94.0% | 80.3% |
| XIV(a) | 83% | 33.3 | 32.7 | −45 (−60) | 22.2 | 24.5 | — | — | 26.9 | 38.5 | 112.1 | 93.0% | 90.2% |
| XIV(b) | 88.5% | 33.3 | 32.7 | −70 (−75) | — | — | 14.8 | 34.0 | 51.9 | 69.7 | 170.4 | 86.0% | 76.4% |

(A) The temperatute at which the deoxygenation started is given in parenthesis

EXAMPLE XV

One-pot synthesis of
7β-amino-3-(5-methyl-1,3,4-thiadiazol-2-yl-thiomethyl)-3-cephem-4-carboxylic acid starting from
7β-phenylacetamido-3-methyl-3-cephem-4-carboxylic acid 1β-oxide Continuously operating in nitrogen atmosphere 102.6 g of 7β-phenylacetamido-3-methyl-3-cephem-4-carboxylic acid 1β-oxide (purity 97.5% by weight according to HPLC-assay) were converted in the corresponding trimethylsilyl ester according to the method described in EPC application No. 0 043 630 employing 2 1 of dichloromethane, 35.5 ml of hexamethyl disilazane, 10 g of succinimide and 0.075 g of saccharine. The reaction mixture obtained was brominated under irradiation according to the method described in EPC applications No. 0 034 394 and No. 0 015 629, using 74 g of N-bromo-succinimide and 2.64 g of sulfaminic acid. The reaction mixture obtained was selectively debrominated according to the method described in EPC application No. 0 001 149, using 20 ml of tributyl phosphite.

In the mean time 40 g of 5-methyl-1,3,4-thiadiazol2-yl-thiol were converted in the corresponding trimethylsilyl thioether according to the process described in EPC application No. 0 043 630 employing 200 ml of dichloromethane, 50 ml of hexamethyldisilazane and 0.1 g of saccharine.

According to the process described in EPC application No. 0 047 560 the latter solution containing the silylated thiol was added at 5° C. to the former solution, followed by stirring during 5.5 h at 5° C.

The reaction mixture obtained was cooled to −52° C., followed by introduction of sequentially 6 ml of N,N-dimethylformamide, 42 ml of cis-cyclooctene and 68 g of phosphorus pentachloride. After stirring for 15 minutes at −48° to −52° C., 64 ml of N,N-dimethyl aniline and 60 g of phosphorus pentachloride were added at −50° C. followed by 2 h stirring at −50° C. 200 ml of precooled isobutanol were introduced slowly at maximally −45° C. followed by 1 hour stirring at −45° C.

The reaction mixture obtained was treated with 400 ml of water and stirred during 15 minutes at −5° C. The aqueous phase was separated from the organic layer. The latter one was extracted with 100 ml of water. The aqueous solutions combined were diluted with 400 ml of acetone, whereupon at 10° C. 25% sodiumhydroxide was added slowly in 30 min to give pH 3. The preparation was stored during 1 hour at 0° to 5° C. The resulting precipitate was collected by filtration, washed sequentially with 100 ml of iced water, 100 ml of 1:1 acetone-water and 200 ml of acetone. After drying in vacuo the product obtained weighed 55.5 g. According to HPLC-assay the isolated product contained 85.5% by weight of 7$\beta$-amino-3-(5-methyl-1,2,4-thiadiazol-2-yl-thiomethyl)-3-cephem-4-carboxylic acid. Among the impurities were 0.5% by weight of 7$\beta$-amino-3-methyl-3-cephem-4-carboxylic acid. In view of the content the overall yield therefore was about 48%.

Example XVI

One-pot synthesis of 7$\beta$-amino-3-(1-methyl-(1H)tetrazol-5-yl-thiomethyl)-3-cephem-4 carboxylic acid starting from 7$\beta$-phenylacetamido-3-methyl-3-cephem-4-carboxylic acid 1$\beta$-oxide In dry atmosphere 5 l of dichloromethane was removed by boiling from a mixture of 3.078 kg of the sulphoxide (purity 97.5% by weight), 0.3 kg of succinimide, 2.3 g of saccharine and 612 l of dichloromethane. Introduction of 1065 ml of hexamethyl disilazane was followed by boiling at reflux until a clear solution was achieved.

After introduction of 80 g of sulphaminic acid and 2.225 kg of N-bromo-succinimide the mixture was irradiated during 2 h at 0° to −5° C. according to the process of EPC application No. 0 034 394. Stirring was provided for by recycling. Subsequently 0.6 l of tributyl phosphite was added at −10° C., followed by 15 min. stirring at -5° C.

1.29 kg of anhydrous sodium 1-methyl-(5H)tetrazol-5yl-thiolate were added, whereupon the mixture was stirred for 1 h at 0° to −5° C.

After cooling to −53° C. 180 ml of N,N-dimethylformamide and 1.26 l of cis-cyclooctene were given to the reaction mixture, whereupon 1.8 kg of phosphorus pentachloride were introduced gradually with stirring during about 15 min., while maintaining the internal temperature close to −53° C. The resulting mixture was stirred during 30 min. at −48° to −52° C. 1.92 l of N,N-dimethyl aniline and 1.8 kg of phosphorus pentachloride were added in about 15 min. followed by 2 h stirring at −47° to −45° C.

While maintaining the reaction temperature between −42° and −40° C., 6 l of precooled isobutanol were added in about 10 min. followed by 1 h stirring. The reaction mixture was transferred to another vessel and therein treated with in total 12 l of water during 10 min. at finally −5° C. The aqueous phase was separated from the organic phase. The latter phase was extracted with in total about 3 l of cold water. The aqueous phases combined were diluted with 6 l of acetone. The resulting solution was at about 25° C. introduced gradually with stirring in a mixture of 6 l of water and 6 l of acetone, while continuously adding 25% sodium hydroxide in water to maintain pH 3. After one hour additional stirring at 10° C. the preparation was left standing at about 10° C. during 1.5 h. The crystalline product was collected by filtration, washed sequentially with 6 l of iced water, 3 l of 1:1 acetone-water and 6 l of acetone. After drying in a ventilated cupboard the product obtained weighed 1.704 kg. According to HPLC-assay the isolated product contained 89.2% by weight of 7$\beta$-amino-3-(1-methyl-(1H)tetrazol-5-ylthiomethyl)-3-cephem-4-carboxylic acid. Taking into account the actual contents of the starting sulphoxide and the final product the overall yield therefore was 53.7%. Among the impurities were about 1.5% by weight of each 7$\beta$-amino-3-methyl-3-cephem-4-carboxylic acid and 7$\beta$-amino-3-(1-methyl-(1H)tetrazol-5-ylthiomethyl)-3-cephem-4carboxylic acid 1$\beta$-oxide.

EXAMPLE XVII

Preparation of 7$\beta$-amino-3-(pyridinium-methyl-methyl)-3-cephem-4carboxylate dihydrochloride from 7$\beta$-phenylacetamido-3-(pyridinium-1-yl-methyl)-3-cephem-4-carboxylate 1$\beta$-oxide The crude starting material was obtained by interruption of a process similar to the one described in Example XV employing a suitable excess of pyridine instead of the silylated thiol used therein.

17.0 g of this product containing 33 mmol of compound in view of 82.5% purity by weight was suspended in 200 ml of dichloromethane. Due to the presence of a considerable amount of water and other hydroxylic impurities 16.9 ml (132 mmol) of N,N-dimethyl aniline and 17.0 ml (133 mmol) of trimethyl chlorosilane had to be introduced to dissolve the product during 90 minutes stirring at 30°-32° C. in nitrogen atmosphere.

The resulting solution was cooled down to −40° C. followed by sequential introduction of 4.7 ml (36.3 mmol) of cis-cyclooctene, 0.6 ml of N,N-dimethylformamide and 8.61 g (41.3 mmol) of phosphorus pentachloride. After stirring during 20 minutes, 4 ml (31.5 mmol) of N,N-dimethyl aniline and 12.9 g (62 mmol) of phosphorus pentachloride were added followed by 70 minutes stirring at −35° C. The temperature was lowered to −55° C., whereupon 50 ml of 1,3-dihydroxypropane were added. Stirring was continued for 60 minutes at −10° C. The mixture obtained was diluted with 50 ml of toluene and subsequently evaporated in vacuo, finally at 1 mm Hg. The residue was dissolved in methanol, whereupon 500 ml of ethyl acetate was added gradually while stirring vigorously. Cooling in an icebath during 1 hour afforded a precipitate, which was collected by filtration and subsequently triturated in 100 ml of ethyl acetate. After solvent removal by filtration the solid was dissolved in methanol. 200 ml of isopropanol were added, followed by concentration in vacuo to a volume of about 100 ml. The suspension obtained was subjected to centrifugation. The residual solid was two times washed with 50 ml of isopropanol by centrifugation. The final product was dried in vacuo. Obtained were 12.5 g of 7β-amino-3-(pyridinium-1-yl-methyl)-3-cephem-4-carboxylate dihydrochloride, amounting to a yield of 81% in view of a purity of 78% by weight according to HPLC assay. The impurity of the final product was to considerable extent due to the presence of isopropanol and 1,3-dihydroxypropane as was apparent from the PMR spectrum PMR ($D_2O$, δ-values in ppm, 60 Mc, int. ref. 2,2-dimethylsilapentane-5-sulphonate): 3.21, 3.52, 3.66 and 3.96 (AB-q, J=18.5 Hz, 2H); 5.20 and 5.29 (d, J=5.2 Hz, 1H); 5.34 and 5.42 (d, J=5.2 Hz, 1H); 5.29, 5.54, 5.75 and 5.99 (AB-q, J=14.7 Hz, 2H); 7.97 to 9.14 (m, 5H).

IR (KBr-disc, values in $cm^{-1}$): 3400, 1785, 1715, 630, 1485, 1400, 1210.

EXAMPLE XVIII

Preparation of
7β-amino-3-(1-(2-dimethylamino)ethyl-(1H)tetrazol-5-yl-thio-methyl)-3-cephem-4-carboxylic acid hydrochloride from a solution of crude trimethylsilyl 7β-phenylacetamido-3-bromomethyl-3-cephem-4-carboxylate 1β-oxide A process was carried out as described in Example XV giving after the debromination reaction a solution of 5.59 mmol of trimethylsilyl phenylacetamido-3-bromomethyl-3-cephem-7β-4-carboxylate 1β-oxide in 65 ml of dichloromethane.

In nitrogen atmosphere and while stirring at −10° C., 0.12 ml of N,N-dimethylformamide and 1.88 g (9.9 mmol) of ammonium 1-(2-dimethylamino)ethyl-(1H)tetrazol-5-yl-thiolate were introduced, followed by 45 minutes stirring wherein the temperature of the mixture was allowed to rise to about 10° C. The resulting reaction mixture was cooled down to −55° C., followed by sequential addition of 0.94 ml (7.26 mmol) of ciscyclooctene, 0.14 ml (1,1 mmol) of N,N-dimethyl aniline and 2.0 g (9.5 mmol) of phosphorus pentachloride. The mixture was stirred during 30 minutes at −48° C., followed by sequential introduction of 2.0 ml (15.8 mmol) of N,N-dimethyl aniline and 2.0 g (9.5 mmol) of phosphorus pentachloride.

The mixture was stirred for 135 minutes at −45° C., followed by dropwise addition of 6.7 ml of isobutanol and 90 minutes stirring at −40° C. 25 ml of water were added. After 10 minutes stirring at −5° C., the layers were separated and the organic layer extracted with 5 ml of water. The water layers combined were washed with 15 ml of dichloromethane. The organic layers were discarded and the aqueous solution treated with triethylamine under a layer of 25 ml of ethyl acetate until the pH had been raised to 6.0. After separation, the organic layer was discarded and the aqueous layer treated with 6N hydrochloric acid until pH 3.2, whereupon activated carbon was added, followed by stirring at 0°–5° C. and filtration. The filtrate was concentrated in vacuo until appearance of a precipitate. About 100 ml of ethanol were introduced gradually to effect substantially complete precipitation, whereafter stirring was continued during 30 minutes at 3° C. The solid was collected by filtration, washed respectively with ethanol and acetone, and dried in vacuo.

Isolated were 1.70 g of 7β-amino-3-(1-(2-dimethylamino)ethyl-(1H)tetrazol-5-yl-thiomethyl-3-cephem-4-carboxylic acid hydrochloride of according to HPLC assay 87.3% purity by weight. The overall yield over three steps therefore amounts to about 63%, while the yield over the whole sequence starting from 7β-phenylacetamido-3-methyl-3-cephem-4-carboxylate 1β-oxide will be in the vicinity of 40%.

PMR ($D_2O$, δ-values in ppm, 60 Mc, int. ref. 2,2-dimethylsilapentane-5-sulphonate): 3.07 (s, 6H); 3.86 (t, J=6 Hz, 2H); 3.83 (s, 2H); 4.32 (s, 2H); 5.02 (t, J=6 Hz, 2H); 5.17 (d, J=5.2 Hz); 5.31 (d, J =5.2 Hz, 1H).

IR (KBr-disc, values in $cm^{-1}$): 3360, 1802, 1618, 530, 1410, 1345, 1285.

EXAMPLE XIX

Preparation of a monosodium salt of
7β-amino-3-(1-sulfomethy-1-(1H)tetrazol-5-yl-thiomethyl)-3-cephem-4-carboxylic acid from a solution of crude trimethylsilyl
7β-phenylacetamido-3-bromomethyl-3-cephem-4-carboxylate 1β-oxide A process was carried out as described in Example XV. Silylation, bromination and debromination afforded 323 g of a mixture containing 20.24 mmol of trimethylsilyl 7β-phenylacetamido-3-bromomethyl-3-cephem-4-carboxylate 1β-oxide according to HPLC assay.

In nitrogen atmosphere and with stirring, 7.8 g (31.85 mmol) of dry disodium salt of 1-sulfomethyl-1(1H)tetrazol-5-yl-thiol was added at −5° C. in 2 minutes to this mixture, followed by 60 minutes additional stirring at −10° to 0° C.

During cooling the resulting mixture to −60° C. were introduced 0.3 ml (2.3 mmol) of N,N-dimethyl aniline, 0.3 ml of N,N-dimethylformamide and 3.4 ml (26.1 mmol) of ciscyclooctene. Addition of 7.2 g (34.6 mmol) of phosphorus pentachloride was followed by 40 minutes stirring at −60° C., whereupon 7.2 ml (56.8 mmol) of N,N-dimethyl aniline and 7.2 g (34.6 mmol) of phosphorus pentachloride were introduced sequentially.

The mixture obtained was stirred for 2 hours at −40° to −50° C., followed by gradual introduction of 24 ml of isobutanol and 1 hour stirring at −40° C. 45 ml of water were added and the resulting mixture was stirred vigorously at −9° to −15° C. during 15 minutes. At a temperature of slightly below 0° C. about 25 ml of 4N NaOH were added with stirring to the very acidic mixture to give at 0° C. a pH of about 0.2. The lightly turbid solution was clarified by filtration with the help of filter-aid. The resulting layers were separated and the organic phase tracted with 12 ml of cold water. The aqueous layers were separately washed with the same portion (25 ml) of dichloromethane. The organic layers were discarded and the combined aqueous solution (about 90 ml) was treated in the cold with an aqueous solution of 0.5 g of sodium bisulphite, whereupon 200 ml of methanol were added with stirring, while at the same time introducing about 25 ml 4N NaOH and thereby increasing the pH from about 0.5 to 4.0 at about 10° C. The mixture obtained was left standing for 16 hours at 3° C., whereupon the precipitate formed was collected by filtration, washed with 70% methanol and acetone and dried in vacuo.

Isolated were 7.73 g of the monosodium salt of 7β-amino-3-(1-sulfomethyl-(1H)tetrazol-5-yl-thiomethyl)-3-cephem-4-carboxylic acid of according to HPLC assay 76% purity by weight. The yield over three steps therefore was 67.5%.

PMR (D$_2$O+NaHCO$_3$, δ-values in ppm, 60 Mc, int. ref. 2,2-dimethylsilapentane-5-sulphonate): 3.21, 3.51, 3.64 and 3.93 (AB-q, J=18 Hz, 2H); 3.95, 4.18, 4.32 and 4.54 (AB-q, J=13.5 Hz, 2H); 4.71 (d, J=4.5 Hz, 1H); 4.99 (d, J=4.5 Hz, 1H); 5.51 (s, 2H).

IR (KBr-disc, values in cm$^{-1}$): 1800, 1615, 1530, 1405, 1340, 1220, 1040, 995 and 590.

EXAMPLE XX

Deoxygenation of 7β-phenylacetamido-3-methyl-3-cephem-4carboxylic acid 1β-oxide via its trimethylsilyl ester employing variable conditions The results collected in Table III reflect inter alia the influence of catalysts on the yield. Most of the experiments, i.e. no. 1-12 and 18 involved the following standard silylation procedure as well as the subsequent reduction procedure. In order to remove moisture azeotropically, 15 ml of dichloromethane were distilled off from a mixture consisting of 6.93 g (19.40 mmol in view of 97.5% purity by weight according to HPLC assay), 5 mg of saccharine and 125 ml of dichloromethane. Continuously operating under a blanket of nitrogen 2.42 ml (11.6 mmol or 1.29 trimethylsilyl equivalent) of hexamethyl disilazane were added dropwise in 15 minutes to the gently boiling suspension. Boiling was continued during 205 minutes, whereupon the temperature was lowered to −60° C., followed by introduction of 22 mmol of the olefine (38.8 mmol in entry 4), eventually a catalyst according to Table III and 4.8 g (23 mmol) of phosphorus pentachloride with as exception entry 18, wherein succinimide was introduced at the start of the silylation procedure. After stirring at −45° C., 20 ml of water were aded slowly and carefully, followed by 15 minutes stirring at −10° C. After addition of 40 ml of toluene stirring was continued during 3 hours at 0° C. The precipitate formed was collected by filtration, washed with water and toluene, and dried in vacuo. The actual isolation yield was determined by HPLC assay. In the same way it was determined how much of 7β-phenylacetamido-3-methyl-3-cephem-4-carboxylic acid was still present in the combined mother liquors.

The silylation procedure used, which was chosen to reveal the effect of catalysis, is definitely not ideal in the sense of realizing optimum conversion yields, since, except for entry 18, the excess of the silylation agent which may hinder the reaction with phosphorus pentachloride was not destroyed, nor were remnants of ammonia incapacitated by e.g. amidosulphonic acid. The result of entry 18 indicates the positive effect of the removal of excess silylating agent. That this silylation procedure is not ideal is further indicated by the unusual amount of product still present in the mother liquor, even in the case of using cis-cylooctene. That cis-cyclooctene, which under practical conditions is an agent of choice, is not always among the best and/or fastest reacting agents is revealed by a comparison between the results of duplicate entries 1-2 with those of at the one hand entries 3, 4 and at the other hand entries 10 and 12. Entries 5-9 in comparison with entries 1-2 definitely show catalysis by N,N-dimethyl formamide and N,N-dimethyl aniline, and by to smaller extent triethyl amine. That a possible catalysing effect of pyridine is compensated by retardation through complex formation with phosphorus pentachloride is indicated by the result of entry 5, while complexation of this agent with quinoline apparently does not fully mask the catalysing ability of this base.

Entries 13-17 relate to the following experimental conditions:

In the case of silylating with pyridine and trimethyl chlorosilane, these agents are sequentially introduced with an interval of five minutes at 0° C. into the stirred suspension of 19.4 mmol of the starting material in 80 ml of dichloromethane, followed by 30 minutes stirring at ambient temperature. Replacing pyridine for triethylamine, introduction of the agents occurred at −10° C. in the same way, followed by 60 minutes stirring at −10° C. The subsequent manipulations were carried out as indicated above.

The results of entries 13-17 show very clearly, that even when matched with an equal excess of trimethyl chlorosilane, pyridine can only be used advantageously in a low excess. The very good result of entry 16 is possibly indicative for catalysis by the hydrochloric acid salt of pyridine.

Deoxygenation of 7β-phenylacetamido-3-methyl-3-cephem-4-carboxylic acid 1β-oxide (A), via its trimethylester, by phosphorus pentachloride and olefinic compound in dichloromethane at −45° C. employing variable conditions

| Exp. | silylating | olefinic compound (deviations) | reaction time (min) | isolation yield (%) | mother liq. (%) | total (a) conv. (%) | comp. A in reac. mixt. (%) |
|---|---|---|---|---|---|---|---|
| 1. | HMDS/ saccharine | cis-cyclo-octene | 15 | 70.3 | 7.8 | 78.1 | ND |
| 2. | HMDS/ saccharine | cis-cyclo-octene | 15 | 76.0 | 1.7 | 77.7 | ND |
| 3. | HMDS/ saccharine | cis-cyclo-octene | 45 | 76.8 | 8.4 | 85.2 | ND |
| 4. | HMDS/ saccharine | cis-cyclo-octene (2 eq.) | 15 | 71.7 | 13.9 | 85.6 | ND |
| 5. | HMDS/ saccharine | cis-cyclo-octene (+0.2 pyr.) | 15 | 69.4 | 10.5 | 79.7 | ND |
| 6. | HMDS/ saccharine | cis-cyclo-octene | 15 | 75.7 | 7.1 | 82.8 | ND |
| 7. | HMDS/ saccharine | cis-cyclo-octene (+0.1 TEA) | 15 | 69.4 | 13.8 | 83.2 | ND |

-continued

Deoxygenation of 7β-phenylacetamido-3-methyl-3-cephem-4-carboxylic acid 1β-oxide (A), via its trimethylester, by phosphorus pentachloride and olefinic compound in dichloromethane at −45° C. employing variable conditions

| Exp. | silylating | olefinic compound (deviations) | reaction time (min) | isolation yield (%) | mother liq. (%) | total (a) conv. (%) | comp. A in reac. mixt. (%) |
|---|---|---|---|---|---|---|---|
| 8. | HMDS/saccharine | cis-cyclo-octene (+0.1 DMA) | 15 | 74.8 | 14.1 | 88.9 | ND |
| 9. | HMDS/saccharine | cis-cyclo-octene (+0.1 DMF) | 15 | 81.0 | 4.0 | 85.0 | ND |
| 10. | HMDS/saccharine | 1-methyl-cyclohexene | 15 | 70.2 | 14.0 | 84.2 | ND |
| 11. | HMDS/saccharine | cyclohexene | 15 | 64.2 | 6.6 | 70.8 | 13.0 |
| 12. | HMDS/saccharine | 2,3-dimethyl-2-butene | 15 | 73.5 | 11.9 | 85.4 | ND |
| 13. | 1.8 TNCS + 1.8 pyr. | cis-cyclo-octene | 15 | 37.5 | 2.9 | 40.4 | 60.0 |
| 14. | 1.8 TMCS + 1.8 pyr. | cis-cyclo-octene | 120 | 81.2 | 2.3 | 83.5 | ND |
| 15. | 1.13 TMCS + 1.13 pyr. | cis-cyclo-octene | 15 | 78.2 | 2.2 | 80.4 | 14.0 |
| 16. | 1.13 TMCS + 1.13 pyr. | cis-cyclo-octene | 45 | 94.0 | 3.3 | 97.3 | ND |
| 17. | 1.13 TMCS + 1.13 TEA | cis-cyclo-octene | 15 | 81.0 | 4.6 | 85.6 | ND |
| 18. | HMDS/saccharine (+0.35 succinimide) | cis-cyclo-octene | 15 | 74.8 | 9.6 | 84.4 | ND |

(a) Although it is experimentally somewhat more difficult to obtain accurate figures for the percentage of total conversion from the HPLC-analysis of the reaction mixture, those percentages (not shown in the table) nearly always were within 3% absolute from the ones calculated after isolation. Abbreviations: HMDS: hexamethyldisilazane, pyr.: pyridine, quin.: quinoline, TEA: triethylamine, DMA: N,N—dimethyl aniline, DHF: N,N—dimethyl formamide, TMCS: trimethyl chlorosilane.

EXAMPLE XXI

One-pot synthesis of 7β-amino-3-(1-carboxymethyl-(1H)tetrazol-5-yl thiomethyl)-3-cephem-4-carboxylic acid starting from 7β-phenylacetamido-3-methyl-3-cephem-4-carboxylic acid 1β-oxide A process was carried out as described in Example XV. Silylation, bromination and debromination afforded 325 ml of a solution in dichloromethane, containing 26.6 mmol of trimethylsilyl 7β-phenylacetamido-3-bromomethyl-3-cephem-4-carboxylate 1β-oxide.

In the mean time 7.2 g (45 mmol) of 1-carboxy-methyl-(1H)tetrazol-5-yl-thiol, 80 ml of 1,2-dichloroethane, 80 mg of saccharine and 13.6 ml of hexamethyldisilazane were boiled at reflux during 3.5 hours. Evaporation in vacuo afforded trimethylsilyl 5-trimethylsilylthio-(1H)tetrazol-1-yl-acetate as a viscous oil.

In the solution of the silylated 3-bromomethylcephalosporin intermediate were added at 5° C. 0.9 ml of N,N-dimethylformamide and the silylated thiol with the help of a few ml of dry dichloromethane. The resulting mixture was stirred during 5.5 hours at 5° C. in nitrogen atmosphere.

The reaction mixture obtained was cooled to −52° C. followed by introduction of sequentially 0.4 ml of N,N-dimethyl aniline, 5.5 ml of cis-cyclooctene and 9.9 g of phosphorus pentachloride, followed by 30 minutes stirring at −45° C. Subsequently were added 10.2 ml of N,N-dimethyl aniline and 9.9 g of phosphorus pentachloride, followed by 1 hour stirring at −45° C. Between −45° and −35° C. were added slowly 31.5 ml of precooled isobutanol, whereupon the mixture was stirred during 1 hour at −40° C.

Addition of 50 ml of water was followed by 15 minutes stirring at 0° C. The aqueous phase was separated from the organic layer, which was extracted two times with 40 ml of water. The aqueous layers combined were washed twice with dichloromethane and thereafter diluted with 300 ml of methanol. After slow addition of 4N sodium hydroxide to pH 3.4 the preparation was left standing overnight at 0° C. The precipitate formed was collected by filtration. The product was at 0° C. triturated in 12 ml of a 1:1 mixture of methanol and water, collected by filtration, washed with the same mixture, thereafter with acetone, and dried in vacuo to constant weight. The product weighed 7.4 g. According to PMR-assay the isolated product contained 15.74 mmol of the desired compound, which according to titration with sodium hydroxide was an about 3:1 mixture of 7β-amino-3-(1-carboxymethyl-(1H)tetrazol-5-yl-thiomethyl)-3-cephem-4-carboxylic acid and the monosodium salt thereof. The yield on actually present compound therefore was 59.7% when based on the brominated cephalosporin derivative and about 36.8% when based on 7β-phenylacetamido-3-methyl-3-cephem-4-carboxylic acid 1β-oxide. The purity of the product was about 84% by weight.

The title compound, devoid of remaining monosodium salt, was obtained in about 30% overall yield, and with a purity of 95% by weight according to PMR-assay, by dissolution of the crude product in a minimal volume of water with the help of hydrochloric acid to pH 1.4, dilution with three parts of methanol, filtration and addition of sodium hydroxide to pH 2.6. The precipitate was collected by filtration, and washed and dried as indicated above.

PMR (DCO$_2$D, δ-values in ppm, 250 Mc, int. ref. TMS): 3.83, 3.90, 3.90, 3.97 (AB-q, J=18 Hz, 2H); 4.50, 4.55, 4.64, 4.69 (AB-q, J=14 Hz, 2H); 5.43, 5.45, 5.47, 5.49 (AB-q, J about 5 Hz, 2H); 5.50 (s, 2H).

IR (KBr-disc, values in cm$^{-1}$): 1820, 1635, 1550, 1370, 1130, 1080.

Various modifications of the processes of the invention may be made without departing from the spirit or scope thereof and it is to be understood that the invention is intended to be limited only as defined in the appended claims.

What we claim is:

1. In a process for the preparation of 7 β-acylamino-3-substituted-3-cephem-4-carboxylic acid compounds of the formula

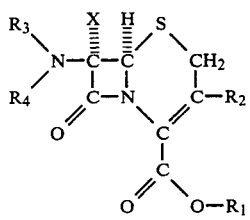

II wherein X is selected from the group consisting of hydrogen, alkoxy of 1 to 4 carbon atoms and alkylthio of 1 to 4 carbon atoms, R$_1$ is a hydroxy protective group, R$_2$ is selected from the group consisting of hydrogen, chlorine, methoxy, trifluoromethyl, vinyl, methyl, and methyl substituted by one member selected from the group consisting of: (a) halogen, (b) protected hydroxy, (c) alkoxy and alkylthio of 1 to 4 carbon atoms, (d) alkanoyloxy and alkanoylthio of 2 to 5 carbon atoms, (e) 1-pyridinium optionally substituted with at least one member of the group consisting of cyano, chloro, dialkylamino with alkyls of 1 to 4 carbon atoms, alkoxy of 1 to 4 carbon atoms, alkoxycarbonyl of 2 to 5 carbon atoms, dialkylcarbamoyl with alkyls of 1 to 4 carbon atoms, hydroxy, carboxy, sulfo, and alkyl of 1 to 4 carbon atoms optionally substituted on the first or second carbon atom thereof with a member selected from the group consisting of dialkylamino with alkyls of 1 to 4 carbon atoms, chloro, cyano, methoxy, alkoxycarbonyl of 2 to 5 carbon atoms, N,N-dimethylcarbamoyl, hydroxy, carboxy and sulfo, and (f) heterocyclic thio optionally substituted on ring carbons with at least one member of the group consisting of cyano, chloro, dialkylamino with alkyls of 1 to 4 carbon atoms, alkoxy of 1 to 4 carbon atoms, alkoxycarbonyl of 2 to 5 carbon atoms, dialkylcarbamoyl with alkyl groups of 1 to 4 carbon atoms, hydroxy, carboxy, sulfo, and alkyl of 1 to 4 carbon atoms optionally substituted on the first or second carbon atom thereof with a member selected from the group consisting of dialkylamino with alkyl of 1 to 4 carbon atoms, chloro, cyano, methoxy, alkoxycarbonyl of 2 to 5 carbon atoms, N,N-dimethylcarbamoyl, hydroxy, carboxy and sulfo, and/or on a saturated ring nitrogen atom with alkyl of 1 to 4 carbon atoms optionally substituted on the first or second carbon atom thereof with a member selected from the group consisting of dialkylamino with alkyls of 1 to 4 carbon atoms, chloro, cyano, methoxy, alkoxycarbonyl of 2 to 5 carbon atoms, N,N-dimethylcarbomoyl, hydroxy, carboxy and sulfo, R$_3$ is acyl of an organic carboxylic acid of 1 to 18 carbon atoms and R$_4$ is hydrogen or R$_3$ and R$_4$ taken together with the nitrogen atom to which they are attached form phthalimido comprising reacting at −70° C. to 0° C. in an inert organic solvent phosphorus pentachloride with a compound of the formula

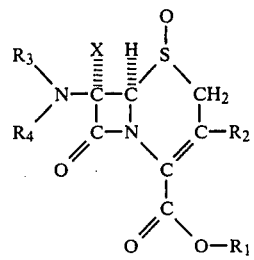

I wherein X, R$_1$, R$_2$, R$_3$ and R$_4$ have the above definition with any hydroxy, carboxy, sulfo and heterocyclic saturated amino groups contained in R$_2$ and R$_3$, optionally being protected by silylation or in the last case also by acylation, the improvement comprising effecting the reaction in the presence of an olefinic compound having at least one carbon-carbon double bond having not more than three hydrogen atoms attached thereto capable of removing chlorine at least in part by addition to a carbon-carbon double bond.

2. The process of claim 1 wherein R$_1$ is selected from the group consisting of trimethylsilyl, dimethylchlorosilyl, dimethylsilyl attached by carboxylate oxygen to an additional cephalosporanyl moiety of formula I, t-butyl, pentachlorophenyl, 2,2,2-trichloro-ethyl, benzhydryl, 4-nitro-benzyl and 4-methoxy-benzyl.

3. The process of claim 1 wherein R$_2$ is an optionally substituted 1-pyridinium group or an optionally substituted 3 heterocyclic thio group of which the heterocyclic radical is selected from the group consisting of pyridine, pyrimidine, pyridazine, pyrrole, imidazole, pyrazole, isoxazole, isothiazole, thiazole, 1,2,3-(1H)triazole, 1,2,4-triazole, 1,2,4- and 1,3,4-oxadiazole, 1,2,4-, 1,3,4-, 1,2,3- and 1,2,5thiadiazole, 1,2,3,4-thiatriazole and (1H)tetrazole linked by a ring carbon atom to the sulfur atom.

4. The process of claim 1 wherein R$_3$ is selected from the group consisting of formyl, alkanoyl of 1 to 18 carbon atoms alkenoyl of 2 to 18 carbon atoms, aroyl of 6 to 12 carbon atoms, heterocyclic carbonyl, aryloxyacetyl, cyanoacetyl, halcacetyl, phenylacetyl, α-hydroxyphenylacetyl, a-carboxyphenylacetyl, α-sulfo-phenylacetyl, α-carboxy-thienylacetyl, α-acylamino-phenylacetyl, α-(substituted)oxyimino-aryl (or -furyl or -thiazolyl) acetyl, optionally having attached to an aromatic or heterocyclic ring substituents selected from the group consisting of chlorine, fluorine, methoxy, cyano, lower alkyl, hydroxy and carboxy.

5. The process of claim 1 wherein R$_3$ and R$_4$ are phthalimido.

6. The process of claim 1 wherein in the starting compound any hydroxy, carboxy and sulfo groups attached to substituents R$_2$ and R$_3$ and a heterocyclic secondary amino group contained in R$_2$ are protected by silylation preferably adjusted in situ or in the last case also by acylation.

7. The process of claim 1 wherein the olefinic compound is a monoolefin or a diolefin having one or both carbon-carbon double bonds in a chain of 3 to 20 carbon atoms or in a ring or 4 to 12 ring carbon atoms, whereby the total number of hydrogen atoms attached to the carbon atoms of a carbon-carbon double bond is not greater than two.

8. The process of claim 7 wherein the monoolefinic or diolefinic compound has one or two non-terminal carbon-carbon double bonds.

9. The process of claim 7 wherein the mono- or diolefinic compounds have one or both carbon atoms of a non-terminal carbon-carbon double bond in a chain or a ring additionally substitute by a straight lower alkyl of 1 to 4 carbon atoms.

10. The process of claim 7 wherein the deoxygenation reaction is carried out at $-60°$ to $-20°$ C.

11. The process of claim 1 wherein the deoxygenation reaction is carried out at $-60°$ to $-20°$ C.

12. The process of claim 1 wherein the substantially inert organic solvent is a halogenated hydrocarbon.

13. The process of claim 11 wherein the solvent is selected from the group consisting of dichloromethane, chloroform, 1,2-dichloroethane and lower alkyl nitrile.

14. The process of claim 1 wherein the deoxygenation reaction is carried out in the presence of a catalyst or additive promoting the chlorine-consuming capacity of the also present olefinic compound.

15. The process of claim 14 wherein that the catalyst or additive employed is a N,N-di(lower) alkyl-formamide, a tertiary amine, or a mixture of a N,N-di(lower) alkyl-formamide and a tertiary amine.

16. The process of claim 15 wherein the catalyst or additive is at least one member selected from the group consisting of N,N-dimethylformamide, N,N-dialkyl-aniline and trialkylamine with alkyls of 1 to 4 carbon atoms.

17. A process for the preparation of $7\beta$-amino-cephalosporanic acid derivatives of the formula

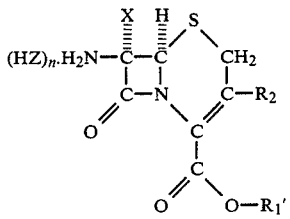

III wherein X is as defined in claim 1, $R'_1$ is hydrogen or a salt forming cation or a "carbon" ester residue as defined in claim 1, $R_2$ is as defined in claim 1, HZ is a salt forming acid and n is 0 or 1 when X is hydrogen or X is not hydrogen and $R'_1$ is hydrogen and n is 1 when X is not hydrogen and $R'_1$ is a "carbon" ester residue comprising subjecting a compound of the formula

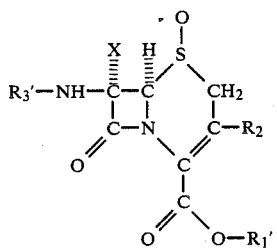

Ia wherein X and $R_2$ are as defined in claim 1, $R'_1$ is hydrogen or a salt forming cation, or a "carbon" ester residue as define in claim 1, $R'_3$ is benzoyl or $R_5$—$CH_2$—CO and $R_5$ is selected from the group consisting of hydrogen, aryl, alkyl, cycloalkyl, alkenyl, aryloxy, alkyloxy, arylthio and alkylthio to (a) a silylation of the cephalosporin 4-carboxyl group to introduce a silyl group when $R'_1$ is hydrogen or a salt forming cation and/or optional protection by silylation and/or acylation of reactive substituents contained in $R_2$ as described in claim 1, (b) subjecting the resulting product to a deoxygenation with phosphorus pentachloride and (c) subjecting the resulting product to a deacylation reaction to split the $7\beta$-acylamino substituent by adding sequentially a suitable tertiary amine and phosphorus pentachloride to form in situ the corresponding imido chloride, and a mono-hydroxyalkane or an alkanediol to form the corresponding imino ether, and finally water for hydrolysis of the imino ether group and of 31 easily removable protective groups the improvement comprising carrying out step (b) in the presence of an olefinic compound having at least one carbon-carbon double bond with no more than two hydrogen atoms attached thereto to remove chlorine predominantly by addition to the carbon-carbon double bond, and optionally in the presence of a catalyst or additive.

18. In a process for the preparation of a $7\beta$-acylamino-3-substituted methyl-cephalosporanic acid derivatives of the formula

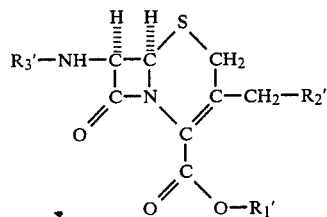

IIa wherein $R'_1$ is hydrogen or a salt forming cation or a "carbon" ester residue, $R'_2$ is selected from the group consisting of (lower), atom (lower)alkylthio, (lower)alkanoyloxy, (lower)alkanoylthio, bromo when $R_1$ is a "carbon" ester residue, 1-pyridinium optionally substituted with at least one member of the group consisting of cyano, chloro, dialkylamino with alkyl of 1 to 4 carbon atoms, alkoxy of 1 to 4 carbon atoms, alkoxycarbonyl of 2 to 5 carbon atoms, dialkylcarbamoyl with alkyls of 1 to 4 carbon atoms, hydroxy, carboxy, sulfo, and alkyl of 1 to 4 carbon atoms optionally substituted on the first or second carbon atom thereof with a member selected from the group consisting of dialkylamino with alkyl of 1 to 4 carbon atoms, chloro, cyano, methoxy, alkoxycarbonyl of 2 to 5 carbon atoms, N,N-dimethylcarbamoyl, hydroxy, carboxy and sulfo, and a heterocyclic thio optionally substituted on ring carbons with at least one member of the group consisting of cyano, chloro, dialkylamino with alkyls of 1 to 4 carbon atoms, alkoxy of 1 to 4 carbon atoms, alkoxycarbonyl of 2 to 5 carbon atoms, dialkylcarbamoyl with alkyl groups of 1 to 4 carbon atoms, hydroxy, carboxy, sulfo, and alkyl of 1 to 4 carbon atoms optionally substituted on the first or second carbon atom thereof with a member selected from the group consisting of dialylamino with alkyl of 1 to 4 carbon atoms, chloro, cyano, methoxy, alkoxycarbonyl of 2 to 5 carbon atoms, N,N-dimethylcarbamoyl, hydroxy, carboxy and sulfo, and-/or on a saturated ring nitrogen atom with alkyl of 1 to 4 carbon atoms optionally substituted on the first or second carbon atom thereof with a member selected from the group consisting of dialkylamino with alkyls of 1 to 4 carbon atoms, chloro, cyano, methoxy, alkoxycarbonyl of 2 to 5 carbon atoms, N,N-dimethylcarbamoyl, hydroxy, carboxy and sulfo, $R'_3$ is selected from the group consisting of formyl, benzoyl and $R_5-CH_2-CO$ and $R_5$ is selected from the group consisting of hydrogen, aryl, alkyl, cycloalkyl, alkenyl, aryloxy, alkyloxy, arylthio and alkylthio comprising subjecting a compound of the formula

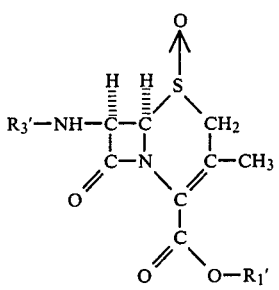

wherein $R'_3$ and $R'_1$ have the above definition to a silylation reaction to introduce a silyl group at the carboxy moiety optionally effected in situ where $R'_1$ is not a "carbon" ester residue and to protect optionally any hydroxy, carboxy and sulfo group contained in $R'_3$, reacting the resulting product with an N-bromo-amide or N-bromo-imide in the presence of light to form the corresponding 3-bromomethyl compound, optionally reacting the latter with triarylphosphite to remove any bromine on the methylene adjacent to the sulfur atom of the dihydrothiazine ring unless it is chosen to prepare and isolate a compound of formula IIa wherein $R'_1$ is a "carbon" ester residue and $R'_2$ is bromo reacting the latter reactant to replace the bromine with an $R'_2$ introducing agent with any hydroxy, carboxy, sulfo and heterocyclic saturated amino group being optionally protected by silylation or in the last case also by acylation and subjecting the resulting product to a deoxygenation reaction with phosphorus pentachloride the improvment comprising effecting the deoxygenation reaction in the presence of an olefinic compound having at least one carbon-carbon double bond with no more than two hydrogen atoms attached thereto to remove chlorine predominantly by addition to the carbon-carbon double bond in the optional presence of a catalyst or additive.

19. The process of claim 18 wherein $R'_1$ is selected from the group consisting of pentachlorophenyl, benzyl, 4-nitro-benzyl, 4-methoxy-benzyl, benzyhydryl, 2,2,2-trichloroethyl and t-butyl 20. A process of claim 18 for the preparation of a compound of the formula

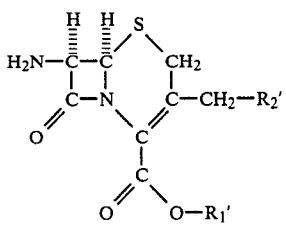

wherein $R'_1$ and $R'_2$ have the definition of claim 17 comprising silylating the carboxy group of a compound of the formula

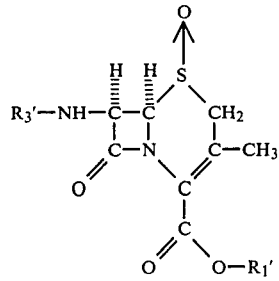

wherein $R'_1$ has the above definition and $R'_3$ is benzoyl or o R -CH2-CO optionally effected in situ where $R'$ is hydrogen or a salt forming cation, brominating the latter in the presence of light, optionally debrominating the latter with trialkylphosphite or triarylphosphite and reacting the latter with a reactant to introducing $R'_2$, and subjecting the products to deoxygenation as in claim 11 and then to a deacylation reaction to split the 7β-acylamino substituent by adding sequentially a suitable tertiary amine and phosphorus pentachloride to form in situ the corresponding imido chloride, and a monohydroxyalkane or an alkanediol to form the corresponding imino ether, and finally water for hydrolysis of the imino ether group and of easily removable protective groups.

21. The process of claim 17 or 18 or 19 wherein $R'_1$ of the compounds of formulae Ia and Ib is hydrogen or a salt forming cation and this compound is converted into the corresponding trimethylsilyl ester.

22. The process of claim 17 or 18 or 20 wherein the multi-step syntheses are performed in a halogenated hydrocarbon.

23. The process of claim. 22 wherein the halogenated hydrocarbon is dichloromethane.

24. The processes of claims 17 or 18 or 20 wherein the deoxygenation is carried out at −65° to −35° C.

25. The process of claim 18 wherein the silylation is effected with a hexasubstituted disilazane for protective silylation of a desacetoxycephalosporanic acid 18-oxide derivative in a halogenated hydrocarbon solvent in the presence of an amout of 0.005 to 5 mol % of a relatively strong silylation catalyst in combination with an amount of 1 to 50 mol % of a silylatable organic compound to assist in the removal and/or incapacitation of remnants of ammonia.

26. The process of claim 25 wherein the silylatable organic compound introduced in the silylation step to assist removal and/or incapacitation of remnants of ammonia is in an amount greater than the amount of the relatively strong silylation catalyst.

27. The process of claim 25 wherein the silylatable organic compound is a relatively weaker silylation catalyst selected from the group consisting of open or saturated cyclic imides, open or saturated cyclic acyl ureas and open or saturate cyclic N-sulfonyl-carbonamides containing an NH between two acyls.

28. The process of claim 26 wherein the silylatable carbon compound is succinimide.

29. The process of claim 17 or 18 or 20 in the deoxygenation step the monoolefinic compound has a non-terminal carbon-carbon carbon double bond in a chain of 4 to 12 carbon atoms optionally substituted at one or both unsaturated carbon atoms with a methyl or ethyl group, or in a carbocyclic ring of 5 to 8 ring atoms optionally substituted at one unsaturated carbon atom with a methyl or ethyl group.

30. The process of claim 29 wherein the monoolefinic compound is cis-cyclooctene.

31. The process of claims 17 or 18 or 20 wherein N,N-dimethylformamide is additionally present in the deoxygenation step.

32. The process of claim 31 wherein the relative amount of N,N-dimethylformamide employed is less than 30 mol % with respect to the introduced amount of the starting compound of formula Ib.

33. The process of claim 18 wherein $R'_3$ is phenylacetamido or phenoxyacetamido and $R'_1$ is trimethylsilyl.

34. The process of claim 18 wherein $R'_1$ is t-butyl and $R'_2$ is bromine or acetoxy.

35. The process of claim 18 wherein the starting material is t-butyl 7β-phenylacetamido-3-methyl-3-cephem-4-carboxylate 1β-oxide to obtain t-butyl 7β-amino-3-acetoxymethyl-cephem-4-car boxylate optionally in the form of an acid addition salt.

36. The of claim 18 wherein on the compounds of formula IIIa $R'_1$ is h or a salt forming cation and $R'_2$ is 1-methyl-(1H)-tetr 5-yl-thio methyl, 1-(2-dimethylamino)ethyl -(1H)-tetrazol-5- 1-sulfomethyl-(1H)-tetrazol-5-yl-thionethyl, 1-carbox (1H)-tetrazol-5-yl-thiomethyl, 1,2,3-(1H)-triazol-5-yl- , 5-methyl-1,3,4-thiadiazol-2-yl-thio-methyl, 1,3 and 2,5-dihydro-6-hydroxy-2-methyl- 1,2,4-triazin-3-yl-thiomethyl optionally comprising external formation of an additional carboxy or sulfo group with an derived from sodium, potassium, or magnesium, ammonia o -lamine, or of the 7β-amino group or an additional group with a strong mineral or organic acid.

37. The proce of claim 36 wherein 7β-amino-3-(1-methyl-(1H)-tetrazol-5-yl)-thiomethyl-3-cephem-4-carboxylic acid is prepared.

* * * * *